(12) United States Patent
Wang et al.

(10) Patent No.: US 6,613,803 B1
(45) Date of Patent: Sep. 2, 2003

(54) CARBOCYCLIC AND HETEROCYCLIC SUBSTITUTED SEMICARBAZONES AND THIOSEMICARBAZONES AND THE USE THEREOF

(75) Inventors: Yan Wang; Sui Xiong Cai, both of San Diego; Nancy C. Lan, S. Pasadena, all of CA (US); John F. W. Keana, Eugene, OR (US); Victor I. Ilyin, Irvine; Eckard Weber, San Diego, both of CA (US)

(73) Assignee: Euro-Celtique S.A. (LU)

( * ) Notice: Subject to any disclaimer, the term of this patent is extended or adjusted under 35 U.S.C. 154(b) by 0 days.

(21) Appl. No.: 09/421,403

(22) Filed: Oct. 21, 1999

Related U.S. Application Data

(63) Continuation of application No. PCT/US98/08004, filed on Apr. 22, 1998.
(60) Provisional application No. 60/062,649, filed on Oct. 22, 1997, and provisional application No. 60/044,530, filed on Apr. 22, 1997.

(51) Int. Cl.[7] .................. A61K 31/17; A61K 31/175
(52) U.S. Cl. ............... 514/583; 514/237.5; 514/255.01; 514/274; 514/311; 514/327; 514/330; 514/351; 514/459; 514/466; 514/590
(58) Field of Search .............. 514/237.5, 255.01, 514/274, 311, 327, 330, 331, 459, 466, 583, 590

(56) References Cited

U.S. PATENT DOCUMENTS

| | | | |
|---|---|---|---|
| 3,139,458 A | 6/1964 | Paquette | 260/554 |
| 3,213,139 A | 10/1965 | Chase et al. | 260/570 |
| 3,251,064 A | 5/1966 | Schultz et al. | 260/294 |
| 3,255,241 A | 6/1966 | Schultz et al. | 260/516 |
| 3,300,484 A | 1/1967 | Pappo | 260/239.5 |
| 3,303,214 A | 2/1967 | Anderson et al. | 260/554 |
| 3,304,323 A | 2/1967 | Fonken et al. | 260/488 |
| 3,324,121 A | 6/1967 | Sprague | 260/247.2 |
| 3,392,171 A | 7/1968 | Fonken et al. | 260/247.7 |
| 3,558,654 A | 1/1971 | Bamford et al. | 260/326.83 |
| 3,712,914 A | 1/1973 | Tilles | 260/479 |
| 4,015,011 A | 3/1977 | Schromm et al. | 424/324 |
| 4,394,514 A | 7/1983 | Kruse | 548/508 |
| 4,454,337 A | 6/1984 | Kruse | 560/22 |
| 4,866,091 A | 9/1989 | Matsuo et al. | 514/471 |
| 4,971,986 A | 11/1990 | Stanek et al. | 514/357 |
| 5,098,466 A | 3/1992 | Anderson et al. | 71/94 |
| 5,102,869 A | 4/1992 | Shiokawa et al. | 514/212 |
| 5,185,026 A | 2/1993 | Drewes et al. | 504/225 |
| 5,236,957 A | 8/1993 | Dostert et al. | 514/620 |
| 5,266,585 A | 11/1993 | Hubele et al. | 514/383 |
| 5,391,577 A | 2/1995 | Dostert et al. | 514/620 |
| 5,502,079 A | 3/1996 | Dostert et al. | 514/620 |
| 5,554,630 A | 9/1996 | Teuber et al. | 514/338 |
| 5,627,180 A | 5/1997 | Missbach | 514/228.8 |
| 5,741,818 A | 4/1998 | Dimmock | 514/590 |
| 5,998,470 A | 12/1999 | Halbert et al. | 514/482 |
| 6,030,974 A | 2/2000 | Schwartz et al. | 514/267 |

FOREIGN PATENT DOCUMENTS

| | | |
|---|---|---|
| BE | 612 755 | 7/1962 |
| BE | 622 079 | 3/1963 |

(List continued on next page.)

OTHER PUBLICATIONS

Dimmock, J.R. et al., "Evaluation of the semicarbazones, thiosemicarbazones and bis–carbohydrazones of some aryl alicyclic ketones for anticonvulsant and other biological properties," *Eur. J. Med. Chem.* 30:303–314, Elsevier Science, Inc. (1995).

(List continued on next page.)

*Primary Examiner*—Richard L. Raymond
(74) *Attorney, Agent, or Firm*—Sterne, Kessler, Goldstein & Fox, P.L.L.C.

(57) ABSTRACT

This invention is related to carbocyclic and heterocyclic substituted semicarbazones and thiosemicarbazones represented by Formula I:

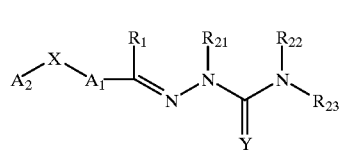

or a pharmaceutically acceptable salt or prodrug thereof, wherein:

Y is oxygen or sulfur; $R_1$, $R_{21}$, $R_{22}$ and $R_{23}$ are independently hydrogen, alkyl, cycloalkyl, alkenyl, alkynyl, haloalkyl, aryl, aminoalkyl, hydroxyalkyl, alkoxyalkyl or carboxyalkyl; or $R_{22}$ and $R_{23}$, together with the N, form a heterocycle; $A_1$ and $A_2$ are independently aryl, heteroaryl, saturated or partially unsaturated carbocycle or saturated or partially unsaturated heterocycle, any of which is optionally substituted; X is one or O, S, $NR_{24}$, $CR_{25}R_{26}$, $C(O)$, $NR_{24}C(O)$, $C(O)NR_{24}$, SO, $SO_2$ or a covalent bond; where $R_{24}$, $R_{25}$ and $R_{26}$ are independently hydrogen, alkyl, cycloalkyl, alkenyl, alkynyl, haloalkyl, aryl, aminoalkyl, hydroxyalkyl, alkoxyalkyl or carboxyalkyl. The invention also is directed to the use of carbocycle and heterocycle substituted semicarbazones and thiosemicarbazones for the treatment of neuronal damage following global and focal ischemia, for the treatment or prevention of neurodegenerative conditions such as amyotrophic lateral sclerosis (ALS), for the treatment and prevention of otoneurotoxicity and eye diseases involving glutamate toxicity and for the treatment, prevention or amelioration of pain, as anticonvulsants, and as antimanic depressants, as local anesthetics, as antiarrhythmics and for the treatment or prevention of diabetic neuropathy and urinary incontinence.

38 Claims, 1 Drawing Sheet

FOREIGN PATENT DOCUMENTS

| | | |
|---|---|---|
| BE | 639 727 | 5/1964 |
| BE | 667 002 | 11/1965 |
| DE | 300 735 A7 | 7/1992 |
| EP | 0 065 485 B1 | 11/1982 |
| EP | 0 299 209 A2 | 1/1989 |
| EP | 0 219 451 B1 | 3/1991 |
| EP | 0 616 807 A1 | 9/1994 |
| WO | WO 92/13846 A1 | 8/1992 |
| WO | WO 94/06758 | 3/1994 |
| WO | WO 95/31448 A1 | 11/1995 |
| WO | WO 96/40628 | 12/1996 |
| WO | WO 95/16433 A1 | 5/1997 |
| WO | WO 98/19674 | 5/1998 |
| WO | WO 98/19674 A3 | 7/1998 |
| WO | WO 98/51290 A2 | 11/1998 |
| WO | WO 98/51290 A3 | 2/1999 |
| WO | WO 99/52522 | 10/1999 |
| WO | WO 00/00120 | 1/2000 |

OTHER PUBLICATIONS

Roufos, I. et al., "A Structure–Activity Relationship Study of Novel Phenylacetamides Which Are Sodium Channel Blockers," *J. Med. Chem.* 39:1514–1520, American Chemical Society (1996).

European Search Report for European Application No. EP 98922043.9, dated May 28, 2001.

Barrett et al., Chemical Abstracts, vol. 134:131540, 2001.*

Lan et al., Chemical Abstracts, vol. 133:305611, 2000.*

American Chemical Society, CAS file CAOLD, see Registry No. 115229–17–9, 1961.

American Chemical Society, CAS file CAOLD, see Registry No. 114399–26–7, 1961.

American Chemical Society, CAS file CAOLD, see Registry No. 107921–04–0, 1958.

American Chemical Society, CAS file CAOLD, see Registry No. 101091–62–7, 1958.

American Chemical Society, CAS file CAOLD, see Registry No. 95135–19–6, 1963.

American Chemical Society, CAS file CAOLD, see Registry No. 94960–09–5, 1963.

American Chemical Society, CAS file CAOLD, see Registry No. 93899–42–4, 1962.

American Chemical Society, CAS file CAOLD, see Registry No. 93651–16–2, 1963.

American Chemical Society, CAS file CAOLD, see Registry No. 92968–95–1, 1964.

American Chemical Society, CAS file CAOLD, see Registry No. 1158–22–1, 1963.

American Chemical Society, CAS file CAPLUS, see Registry No. 36934–63–1 and 36934–64–2, 1972.

American Chemical Society, CAS file CAPLUS, see Registry No. 174521–23–4, 1996.

American Chemical Society, CAS file CAPLUS, see Registry No. 190657–77–3, 1997.

American Chemical Society, CAS file CAPLUS, see Registry No. 144141–11–7, 1992.

American Chemical Society, CAS file CAPLUS, see Registry No. 54291–81–5, 1975.

American Chemical Society, CAS file CAPLUS, see Registry No. 22263–45–2, 1969.

Badische Anilin & Soda–Fabrik A.–G., "Terephthaldialdehyde," *Chemical Abstracts* 65, abstract 5405b (1966). See 5412e.

Bayoumy, B. E.–S. and L. Skulski, "Synthesis of Some New Diaryl Sulphides and Diaryl Sulphones Containing 1,2,3–Thiadiazole Moiety," *Bull. Pol. Acad. Sci. Chem.* 39:455–458 (1991).

Beilstein Informationgesellschaft GmbH, see Belstein Registry No. 2542223, 1989.

Beilstein Informationgesellschaft GmbH, see Belstein Registry No. 1890700, 1989.

Beilstein Informationgesellschaft GmbH, see Belstein Registry No. 3400167, 1990.

Beilstein Informationgesellschaft GmbH, see Belstein Registry No. 3400193, 1990.

Beilstein Informationgesellschaft GmbH, see Belstein Registry No. 3410343, 1953.

Beilstein Informationgesellschaft GmbH, see Belstein Registry No. 3419487, 1990.

Beilstein Informationgesellschaft GmbH, see Belstein Registry No. 3421220, 1990.

Beilstein Informationgesellschaft GmbH, see Belstein Registry No. 3436628, 1952.

Beilstein Informationgesellschaft GmbH, see Belstein Registry No. 3396690, 1990.

Beilstein Informationgesellschaft GmbH, see Belstein Registry No. 3389800, 1990.

Beilstein Informationgesellschaft GmbH, see Belstein Registry No. 3417848, 1990.

Beilstein Informationgesellschaft GmbH, see Belstein Registry No. 3422330, 1990.

Beilstein Informationgesellschaft GmbH, see Belstein Registry No. 3449771, 1990.

Beilstein Informationgesellschaft GmbH, see Belstein Registry No. 3382967, 1990.

Beilstein Informationgesellschaft GmbH, see Belstein Registry No. 3347507, 1990.

Beilstein Informationgesellschaft GmbH, see Belstein Registry No. 3468481, 1990.

Beilstein Informationgesellschaft GmbH, see Belstein Registry No. 3468486, 1990.

Beilstein Informationgesellschaft GmbH, see Belstein Registry No. 3508814, 1990.

Beilstein Informationgesellschaft GmbH, see Belstein Registry No. 5349918, 1993.

Beilstein Informationgesellschaft GmbH, see Belstein Registry No. 3532377, 1990.

Beilstein Informationgesellschaft GmbH, see Belstein Registry No. 3178769, 1990.

Demetresco, C. et al., "p–Alkoxyphenyl p–substituted–phenyl sulfone series. III. Derivatives with potential pharmacodynamic action," *Chim. Ther.* 3:343–347 (1968). [In French].

Demetresco, C. et al., "p–Alkoxyphenyl p–substituted–phenyl sulfone series. III. Derivatives with potential pharmacodynamic action," *Chemical Abstracts* 70, abstract 106164s (1969).

English language translation of Ito, G., "Synthesis of Guanidine Compounds of Diphenyl Ethers. I.," *Pharm. Bull. (Tokyo)* 5:397–400 (1957).

English language translation of Ito, G., "Synthesis of Guanidine Compounds of Diphenyl Ether II. A New Synthesis of Diphenyl Ether Aldehyde According to Sommelet and Experiments with Methylguanidine Derivatives (1).," *Pharm. Bull. (Tokyo)* 5:401–405 (1957).

English language translation of Julia, M.M. and M. Baillarge, "Plant Growth Factors. IV. Some Substituted p–Phenoxy–phenylacetic Acids," *Bull. Soc. Chim. Fr.,* Fifth Series. 20:644–647 (1953).

English language translation of Kimoto, S. et al., "Syntheses of Compounds Allied to Chloramphenicol I.," *Yakugaku Zasshi (J. Pharm. Soc. Japan)* 72:496–497 (1952).

English language translation of Kimoto, S. et al., "Studies on the Friedel–Crafts Reaction in Diphenyl Ether Derivatives. VI. Reaction of Monochlorodiphenyl Ether and Acetyl Chloride," *Yakugaku Zasshi (J. Pharm. Soc. Japan)* 74:358–360 (1954).

English language translation of Tomita, M. et al., "Synthesis of Aldehyde Derivatives Containing a Diphenyl Ether Unit," *Yakugaku Zasshi (J. Pharm. Soc. Japan)* 75:1021–1023 (1955).

Faltis,F. et al., "Biscoclaurine Alkaloids. Constitution of Chondodendrine and Trilobine," *Chem. Ber.* 74:79–97 (1941). [In German].

Faltis,F. et al., "Biscoclaurine Alkaloids. Constitution of Chondodendrine and Trilobine," *Chemical Abstracts 35,* abstract 5121f (1941).

Fujikawa, F. et al., "The Synthesis of Depsidones. I.," *Yakugaku Zasshi (J. Pharm. Soc. Japan)* 83:1172–1174 (1963). [In Japanese].

Fujikawa, F. et al., "Syntheses of Depsidones. I.," *Chemical Abstracts 60,* abstract 10685d (1964).

Gorbacheva, I.N. et al., "Synthesis of Substituted Diphenyl Ethers," *J. Gen. Chem. U.S.S.R.* 25:2259–2263 (1955).

Harington, C.R., "Chemistry of Thyroxine. II. Constitution and Synthesis of Desiodo–Thyroxine," *Biochem. J.* 20:300–313 (1926).

Harington, C.R. and R.V. Pitt Rivers, "A New Synthesis of Thyronine," *J. Chem. Soc.* 1101–1103 (1940).

Ito, G., "Synthesis of Guanidine Compounds of Diphenyl Ether II. A New Synthesis of Diphenyl Ether Aldehyde According to Sommelet and Experiments with Methylguanidine Derivatives (1).," *Pharm. Bull. (Tokyo)* 5:401–403 (1957). [In German].

Julia, M.M. and M. Baillarge, "Plant Growth Factors. IV. Some Substituted p–Phenoxy–phenylacetic Acids," *Bull. Soc. Chim. Fr.,* Fifth Series. 20:644–647 (1953). [In French].

Kimoto, S. et al., "Syntheses of Allied Compounds of Chloramphenicol I.," *Yakugaku Zasshi (J. Pharm. Soc. Japan)* 72:496–497 (1952). [In Japanese].

Kimoto, S. et al., "Studies on the Friedel–Crafts Reaction in Diphenyl Ether Derivatives. VI. Reaction of Monochlorodiphenyl Ether and Acetyl Chloride," *Yakugaku Zasshi (J. Pharm. Soc. Japan)* 74:358–360 (1954). [In Japanese].

Nerurkar, J.J. et al., β–Arylglutaconic acids. IV. Synthesis of crotono– and valerolactones of β–arylglutaconic and glutaric acids. *J. Org. Chem.* 25:1491–1495 (1960).

Ochiai, E. and Y. Tamai, "Friedel–Crafts Reaction of Diphenyl Ethers with Succinic Acid Chloride," *Itsuu Kenkyusho Nempo.* 12:39–41 (1962). [In German].

Ochiai, E. and Y. Tamai, "Friedel–Crafts Reaction of Diphenyl Ethers with Succinic Acid Chloride," *Chemical Abstracts 59,* abstract 7414b (1963).

Rubinchik, M.A. and O.N. Tolkachev, "Study of the antiprotozoal activity of compounds of a group of diphenyl ethers and some nitrostyrenes," *Med. Parazitol. Parazit. Bolezni* 45:531–536 (1976). [In Russian].

Rubinchik, M.A. and O.N. Tolkachev, "Study of the antiprotozoal activity of compounds of a group of diphenyl ethers and some nitrostyrenes," *Chemical Abstracts 86,* abstract 115615x (1977).

Samaritoni, J.G. et al., "Methylene Group Modifications of the N–(Isothiazol–5–yl)phenylacetamides. Synthesis and Insecticidal Activity," *J. Agric. Food Chem.* 47:3381–3388 (Aug. 1999).

Tomimatsu, T. and Y. Kano, "Studies on the Alkaloids of *Thalictrum Thunbergii.* XIII. Structures of Thalicberine and O–Methylthalicberine," *Yakugaku Zasshi (J. Pharm. Soc. Japan)* 83:153–158 (1963). [In Japanese].

Tomimatsu, T. and Y. Kano, "Alkaloids of *Thalictrum thunbergii.* XIII. Structure of thalicberine and O–methylthalicberine. 5.," *Chemical Abstracts 59,* abstract 3971b (1963).

Tomita, M. et al., "Syntheses of Aldehyde Derivatives Containing a Diphenyl Ether Nucleus," *Yakugaku Zasshi (J. Pharm. Soc. Japan)* 75:1021–1023 (1955). [In Japanese].

Vichkanova, S.A. et al., "Structure and antituberculous activity of some diphenyl ethers," *Farmakol. Toksikol. (Moscow)* 37:711–715 (1974). [In Russian].

Vichkanova, S.A. et al., "Structure and antituberculous activity of some diphenyl ethers," *Chemical Abstracts 82,* abstract 106878a (1975).

Volynskaya, E.M. et al., "Monophosphonium salts and monophosphoranes based on 4,4'–diacetylbiphenyl and its derivatives," *Zh. Obshch. Khim.* 42:986–992 (1972). [In Russian].

Volynskaya, E.M. et al., "Monophosphonium salts and monophosphoranes based on 4,4'–diacetylbiphenyl and its derivatives," *Chemical Abstracts 77,* abstract 101775b (1972).

Kolb, V.M., et al., "Abnormally High IR Frequencies for the Carbonyl Group of Semicarbazones of the Benzaldehyde and Acetophenone Series," *J. Org. Chem.* 54:2341–2346, The American Chemical Society (1989).

Norwegian Search Report for Patent Application No. 1999 5094, dated Sep. 19, 2001.

Hungarian Novelty Search Report for Patent Application No. P0001297, dated Oct. 25, 2001.

Missbach, M., "Szubsztituált tioszemikarbazon tionszármazékok, eljárás előállításukra és ezeket tartalmazó gyógyszerkészítmények," Publication No. 71609 of Appl. No. P9502055 (1996).

Leippe, M.M. and Anderson, R.J., "Hatóanyagként szubsztituált szemikarbazon– vagy tioszemikarbazon–számazékokat tartalmazó herbicid szer, valamint eljárás a vegyületek előállítására," Publication No. 43939 of Appl. No. P8603611 (1988).

Baltzly, R. et al., "2,4–Diamino–5–[4'–fluoro–3'–halogenophenyl]pyrimidines," *J. Org. Chem.* 26:2353–2355 (1961).

Bensimon et al., "A Controlled Trial of Riluzole in Amyotrophic Lateral Sclerosis," *New Engl. J. Med.* 330:585–591 (1994).

Brown et al., "Neuroprotective Properties of Lifarizine Compared with Those of Other Agents in a Mouse model of Focal Cerebral Ischemia," *Brit. J. Pharmacol.* 115:1425–1432 (1995).

Buchan et al., "AMPA Antagonists: Do They Hold More Promise for Clinical Stroke Trials NMDA Antagonists?," *Suppl. I Stroke* 24:148–152 (1993).

Catterall W.A., "Neurotoxins that Act on Voltage–Sensitive Sodium Channels in Excitable Membranes," *Ann. Rev. Pharmacol. Toxicol.* 20:15–43 (1980).

Catterall, W.A., "Common Modes of Drug Action on Na⁺ Channels: Local Anesthetics, Antiarrhythmics and Anticonvulsants," *Trends Pharmacol. Sci.* 8:57–65 (1987).

Catterall, W.A., "Structure and Function of Voltage–Sensitive Ion Channels," *Science* 242:50–61 (1988).

Creveling et al., "Batrachotoxin–Induced Depolarization and [³H]Batrachotoxin–A 20α–Benzoate Binding in a Vesicular Preparation from Guinea Pig Cerebral Cortex," *Mol. Pharmacol.* 23:350–358 (1983).

Denicoff et al., "Efficacy of Carbamazepine Compared with Other Agents: A Clinical Practice Survey," *J. Clin. Psychiatry* 55:70–76 (1994).

Dimmock, J.R. et al., "Evaluation of some Mannich bases of 1–aryl–1–ethanones and related ketones for anticonvulsant activities," *Pharmazie* 46:538–539 (1991).

Dimmock, J.R. et al., "Evaluation of the thiosemicarbazones of some aryl alkyl ketones and related compounds for anticonvulsant activities," *Eur. J. Med. Chem.* 26:529–534 (1991).

Dimmock et al., "Anticonvulsant Activities of Some Arylsemicarbazones Displaying Potent Oral Activity in the Maximal Electroshock Screen in Rats Accompanied by High Protection Indices," *J. Med. Chem.* 36:2243–2252 (1993).

Dimmock, J.R. et al., "Some aryl semicarbazones possessing anticonvulsant activities," *Eur. J. Med. Chem.* 30:287–301 (1995).

Dimmock et al., "(Aryloxy)aryl Semicarbazones and Related Compounds: A Novel Class of Anticonvulsant Agents Possessing High Activity in the Maximal Electroshock Screen," *J. Med. Chem.* 39:3984–3997 (Sep. 1996).

Graham et al., "Neuroprotective Effects of a Use–Dependent Blocker of Voltage–Dependent Sodium Channels, BW619C89, in Rat Middle Cerebral Artery Occlusion," *J. Pharmacol. Exp. Ther.* 269:854–859 (1994).

Graham et al., "A Dose–Response Study of Neuroprotection Using the AMPA Antagonists NBQX in Rat Focal Cerebral Ischemica," *J. Pharmacol. Exp. Therap.* 276:1–4 (Jan. 1996).

Hamill et al., "Improved Patch–Clamp Techniques for High–Resolution Current Recording from Cells and Cell–Free Membrane Patches," *Pfluegers Arch.* 391: 85–100 (1981).

Hunskaar et al., "Formalin Test in Mice, a Useful Technique for Evaluating Mild Analgesics," *J. Neurosci. Method* 14:69–76 (1985).

Ingersoll, A.W. et al., "Extensions of the Leuckart Synthesis of Amines," *J. Amer. Chem. Soc.* 58:1808–1811 (1936).

Ito, G. "Synthese von Guanidinverbindungen des Diphenläthers. I.," *Pharm. Bull.* 5:397–400 (1957).

Ito, G., "Synthesis of guanidine compounds of diphenyl ether. I., " *Chem. Abstracts* 52:Abstract No. 9005i (1958).

Iwasaki et al., "CNQX Prevents Spinal Motor Neuron Death Following Sciatic Nerve Transection in Newborn Rats," *J. Neurological Sci.* 134:21–25 (1995).

Kimoto, S. and K. Asaki, "Studies on the Friedel–Crafts Reaction of Diphenyl Ether Derivatives. II.," *J. Pharm. Soc. Japan* 72: 300–303 (1952).

Kimoto, S. et al., "Studies on the Friedel–Crafts Reaction of Diphenyl Ether Derivatives. III.," *J. Pharm. Soc. Japan* 73:243–244 (1953).

Krall, R.L. et al., "Antiepileptic Drug Development: II. Anticonvulsant Drug Screening," *Epilepsia* 19: 409–428 (1978).

Kuo et al., "Slow Binding of Phenytoin to Inactivated Sodium Channels in Rat Hippocampal Neurons," *Mol. Pharm.* 46:716–725 (1994).

Ohizumi et al., "Specific Inhibition of [³H] Saxitoxin Binding to Skeletal Muscle Sodium Channels by Geographutoxin II, a Polypeptide Channel Blocker," *J. Biol. Chem.* 261:6149–6152 (1986).

Pujol et al., "Pathophysiology of the Glutamatergic Synapsee in the Cochlea," *Acta Otolaryngol (Stockh)* 113:330–334 (1993).

Racine, R.J., "Modification of Seizure Activity by Electrical Stimulation: II. Motor Seizure," *Electroenceph. Clin. Neurophysiol.* 32:281–294 (1972).

Ragsdale et al., "Frequency and Voltage–Dependent Inhibition of Type IIA Na⁺ Channels, Expressed in a Mammalian Cell Line, by Local Anesthetic, Antiarrythmic, and Anticonvulsant Drugs," *Mol. Pharmacol.* 40:756–765 (1991).

List of abstracts concerning SCRIP 1870:8 (1993).

List concerning SCRIP 1773:14 (1992).

Sheardown et al., "AMPA, but not NMDA, Receptor Antagonism is Neuroprotective in Gerbil Global Ischaemia, Even When Delayed 24 h," *Eur. J. Pharmacol.* 236:347–353 (1993).

Skeen, G. et al., "Development of Kindled Seizures Following Electrical Stimulation via the Cornea," *Soc. Neurosci. Abstracts* 16:307, Abstract No. 138.1 (1990).

Stys et al., "Ionic Mechanisms of Anoxic Injury in Mammalian CNS White Matter: Role of Na⁺ Channels and Na⁺—Ca²⁺ Exchanger," *J. Neurosci.* 12: 430–439 (1992).

Taylor et al., "Na⁺ Channels as Targets for Neuroprotective Drugs," *Trends Pharmacol. Sci.* 16:309–316 (1995).

Tomita, M. et al., "Syntheses of aldehyde derivatives containing a diphenyl ether nucleus," *Chem. Abstracts 50*: Abstract No. 4836b (1956).

Ungnade, H.E. and E.F. Orwoll, "The Gattermann Reaction in the Mono–methoxydiphenyl Ethers," *J. Amer. Chem. Soc.* 65: 1736–1739 (1943).

Walker, J., "Experiments on the Synthesis of Potential Cortical Hormone Substitutes. Hydroxycarbonyl Derivatives of Diphenyl Ether and Related Compounds," *J. Chem. Soc.* 347–353 (1942).

Whittemore et al., "Pre–Exposure to L–Homocysteinesulfinic Acid Blocks Quisqualate–Induced Sensitization to L–2–amino–4–phosphonobutanoic Acid," *Eur. J. Pharm.* 192:435–438 (1991).

Wolf, R., "Dosage potentiométrique de mélanges d'acides benzoïque et peroxybenzoïque. Essais pour d'autres mélanges acide–peroxyacide," *Bull. Soc. Chim. France* (5):644–646 (1954).

Wolf, R., "Potentiometric analysis of mixtures of benzoic and peroxybenzoic acids. Analysis of other peroxidic acid mixtures," *Chem. Abstracts 48*:Abstract No. 11247b (1954).

Wrathall et al., "Amelioration of Functional Deficits form Spinal Cord Trauma with Systemically Administered NBQX, an Antagonist of Non–N–methyl–D–aspartate Receptors," *Exp. Neurology* 137: 119–126 (Jan. 1996).

Yeager, G.W. and D.N. Schissel, "A Convenient Method for the Preparation of 4–Aryloxyphenols," *Synthesis (1)*:63–68 (1991).

Horii, Z. and T. Kinouchi, "Ueber die Hydrazone, die sich von ρ–Rhodanphenylhydrazin ableiten. (IV. Mitteilung)," *J. Pharm. Soc. Japan* 57:123–124 (1937).

English Translation of Document AT15, Horii, Z. and T. Kinouchi, "Ueber die Hydrazone, die sich von ρ–Rhodanphenylhydrazin ableitan. (IV. Mitteilung)," *J. Pharm. Soc. Japan* 57:123–124 (1937).

English Translation of Document AS8, Kimoto, S. and K. Asaki, "Studies on the Friedel–Crafts Reaction of Diphenyl Ether Derivatives. II., " *J. Pharm. Soc. Japan* 72:300–303 (1952).

English Translation of Document AT8, Kimoto, S. et al., "Studies on the Friedel–Crafts Reaction of Dipenyl Ether Derivatives. III.," *J. Pharm. Soc. Japan* 73:243–244 (1953).

Derwent WPI, English language abstract of EP 0 065 485 B1 (Document AN1) (1982).

Chauhan, P.M.S., and Chatterjee, R.K., "Synthesis of 1, 3–substituted idoles, 2, 4, 6–substituted–s–trianzines and 4, 5–substituted pyrazoles as possible antifilarial agents," *Ind. J. Chem.* 33B:32–37, Publications & Information Directorate (CSIR) (1994).

Eisa, H.M., et al., "Synthesis of Some Novel Tetrazole Derivatives as Potential Antimicrobial Agents," *Pak. J. Sci. Ind. Res.* 33:417–420, Scientific Information Centre, Pakistan Council of Scientific and Industrial Research (1990).

El–Kashef, H.S., et al., "Selenium Heterocycloes I: Synthesis and Anti–bacterial Activity of Some New 1,2,3–Thia and 1,2,3–Selenadiazoles Containing Sulphonamides," *Egypt. J. Pharm. Sci.* 27:27–35, The National Information and Documentation Centre (NIDOC) (1986).

Iddon, B., et al., "Condensed Thiophen Ring Systems. Part XVI. Derivatives of 11H–[1]Benzothieno[2,3–b][1]benzothiopyran," *J. Chem. Soc. Perkin Trans. I* 21(*Part 3*):2500–2505, The Chemical Society (1974).

Iddon, B., and Lim, B.L., "Metallation and Metal–Halogen Exchange Reactions of Imidazoles," *J. Chem. Soc. Perkin Trans. I* 2:279–283, The Royal Society of Chemistry (1983).

Inomata, K., et al., "Preparation and Diels–Alder Reactions of 3–Substituted 3–Sulfolenes," *Bull. Chem. Soc. Japan* 51:3341–3344, Nippon Kagakukai (1978).

Kada, R., and Kovac, J., "Furan derivatices. LXV. Preparation and ultraviolet spectra of 5–arylthio– and 5–heteroarylthio–2–furaldehydes," *Chem. Zvesti* 29:402–407, Vydavatelstvo Slovenskej Akademie (1975).

Mlochowski, J., "Synteza Aldehydów Chinaldynowych Podstawionych W Położeniu 4," *Rocz. Chem.* 44:1331–1335, Pa´nstwowe Wydawnictwo Naukowe (1970).

Rosnati, V., et al., "Sostituzioni nucleofile su α–clorochetoni. – Nota X. 1–cloro–3–fenilmercapto–2–butanone," *Gazz. Chim. Ital.* 100:591–608, Societa Chimica Italiana (1970).

Saramet, I., "Cercetări asupra ciclizării unor $N_1$–acil–$N_4$–aril–tiosemicarbazide. Sinteza unor noi 1,3,4–tiadiazoli 2,5–disubstituiti de interes terapeutic," *Farmacia* 23:35–42, Centrul de Documentare Medicala (1975).

Саренко, А.С., et al., "Гетероциклическе Аналоги Ксантонов. Хромоно[3, 2–d]–пиразольı," *Khim.–Farm. Zh.* 4:23–26, Izdatelstvo Meditsina (1970).

Satake, Y., et al., "The Basic Studies on Chemotherapy of p–(p'–aminobenzenesulfonyl)–benzaldehyde thiosemicarbazone for Leprosy: Second Report On Metabolites of Thiozamin in vivo," *La Lepro* 38:237–245, Japanese Leprosy Association (1969).

Shafiee, A., et al., "Selenium Heterocycles XXX [1]. Syntheses of 4– (2–*Pyrazinyl*) – 1, 2, 3– Selenadiazole and 4–(2–Pyrazilyl) – 1, 2 3– Thiadiazole," *J. Sci. I. R. Iran* 1:289–293, The National Center for Scientific Research (1990).

Tantawy, A.S., et al., "Synthesis and Biological Testing of Certain 2–(5–substituted–2–thienylthio)benzoic Acid Derivatives," *Il Farmaco* 44:1217–1224, Societa Chimica Italiana (1989).

American Chemical Society, Database CAPLUS, Accession No. 1994:435552, Document No. 121:35552, Chauhan, P.M.S., and Chatterjee, R.K. (1994).

American Chemical Society, Database CAPLUS, Accession No. 1993:409804, Document No. 119:9804, Boettcher, A., et al. (1993).

American Chemical Society, Database CAPLUS, Accession No. 1992:634038, Document No. 117:234038, Luethy, C., and Fisher, R. (1992).

American Chemical Society, Database CAPLUS, Accession No. 1992:106309, Document No. 116:106309, Drewes, M.W., et al. (1992).

American Chemical Society, Database CAPLUS, Accession No. 1991:471490, Document No. 115:71490, Shafiee, A., et al. (1991).

American Chemical Society, Database CAPLUS, Accession No. 1991:408675, Document No. 115:8675, Eisa, H.M., et al. (1991).

American Chemical Society, Database CAPLUS, Accession No. 1991:23865, Document No. 114:23865, Tantawy, A.S., et al. (1991).

American Chemical Society, Database CAPLUS, Accession No. 1987:575955, Document No. 107:175955, El–Kashef, H.S., et al. (1987).

American Chemical Society, Database CAPLUS, Accession No. 1983:405549, Document No. 99:5549, Iddon, B., and Lim, B.L. (1983).

American Chemical Society, Database CAPLUS, Accession No. 1979:103747, Document No. 90:103747, Inomata, K., et al. (1979).

American Chemical Society, Database CAPLUS, Accession No. 1976:70208, Document No. 84:70208, Saramet, I. (1976).

American Chemical Society, Database CAPLUS, Accession No. 1976:17037, Document No. 84:17037, Kada, R., and Kovac, J. (1976).

American Chemical Society, Database CAPLUS, Accession No. 1975:111966, Document No. 82:111966, Iddon, B., et al. (1975).

American Chemical Society, Database CAPLUS, Accession No. 1972:135512, Document No. 76:135512, Satake, Y., et al. (1972).

American Chemical Society, Database CAPLUS, Accession No. 1971:13058, Document No. 74:13058, Sarenko, A.S., et al. (1971).

American Chemical Society, Database CAPLUS, Accession No. 1971:12936, Document No. 74:12936, Rosnati, V., et al. (1971).

American Chemical Society, Database CAPLUS, Accession No. 1970:487761, Document No. 73:87761, Mlochowski, J. (1970).

\* cited by examiner

CARBOCYCLIC AND HETEROCYCLIC SUBSTITUTED SEMICARBAZONES AND THIOSEMICARBAZONES AND THE USE THEREOF

This is a continuation of International Application PCT/US98/08004, with an International Filing Date of Apr. 22, 1998, claiming priority from U.S. Provisional Application Nos. 60/044,530 and 60/062,649, filed Apr. 22, 1997 and Oct. 22, 1997, respectively, now abandoned.

BACKGROUND OF THE INVENTION

1. Field of the Invention

This invention is in the field of medicinal chemistry. In particular, the invention relates to carbocyclic and heterocyclic substituted semicarbazones and thiosemicarbazones, and the discovery that these compounds act as blockers of sodium ($Na^+$) channels.

2. Related Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W.A., Trends Pharmacol. Sci. 8:57–65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham et al., J. Pharmacol. Exp. Ther. 269:854–859 (1994); Brown et al., British J. Pharmacol. 115:1425–1432 (1995); SCRIP 1870:8 (1993); SCRIP 1773:14 (1992)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., J. Neurosci. 12:430–439 (1992)). Thus, they may offer advantages for treating certain types of strokes or neuronal trauma where damage to white matter tracts is prominent. In addition to playing a major role in neurotoxicity involving stroke, glutamate is also a key neurotransmitter which mediates otoneurotoxicity resulting in acute or progressive hearing loss and tinnitus (Pujol et al. Acta Otolaryngol (stockh) 113:330–334 (1993). Therefore, $Na^+$ channel blockers are expected to be effective in preventing and treating otoneurotoxicity by decreasing extracellular gluatmate concentration. Similarly, $Na^+$ channel blockers will be useful for preventing and treating eye diseases involving excitatory toxicity such as glaucoma and CMV retinitis.

Another example of clinical use of a $Na^+$ channel blocker is riluzole. This drug has been shown to prolong survival in a subset of patients with ALS (Bensimm et al., New Engl. J. Med. 330:585–591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, Trends Pharmacol. Sci. 16:309–316 (1995)), and carbamazepine and lamotrigine have been used for the treatment of manic depression (Denicott et al., J. Clin. Psychiatry 55: 70–76 (1994)).

It has been established that there are at least five to six sites on the voltage-sensitive $Na^+$ channels which bind neurotoxins specifically (Catterall, W. A., Science 242:50–61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., Ann. Rev. Pharmacol. Toxicol. 10:15–43 (1980)).

PCT International Published Application WO94/06758 discloses a genus of aryl semicarbazones that have anticonvulsant activity in the maximal electroshock screen when orally administered to rats.

Dimmock et al., J. Med. Chem. 36:2243–2252 (1993) discloses aryl semicarbazones and aryl thiosemicarbazones that display oral activity as anticonvulsants in rats.

PCT International Published Application WO96/40628 discloses semicarbazones represented by Formula IX:

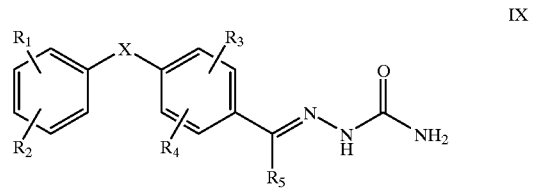

where $R_1$–$R_4$ are independently hydrogen, halogen, $C_{1-9}$ alkyl, $C_{3-9}$ cycloalkyl, cyano, $C_{1-9}$ alkoxy, or $C_{6-10}$ aryloxy; $R_5$ is hydrogen, $C_{1-9}$ alkyl, $C_{3-9}$ cycloalkyl, or $C_{6-10}$ aryl; and X is oxygen or sulfur. The compounds are disclosed to be useful as anticonvulsants.

Dimmock et al., J. Med. Chem. 39:3984–3997 (1996) discloses (aryloxy)aryl semicarbazones that displayed anticonvulsant activities when administered intraperitoneally to mice or orally to rats.

The compounds that are disclosed in each of the aforementioned documents are described as having anticonvulsant activities. However, their mechanism of action had not been elucidated.

SUMMARY OF THE INVENTION

The present invention is related to treating a disorder responsive to the blockade of sodium channels in a mammal suffering from excess activity of said channels by administering an effective amount of a compound of Formula I or Formula IX as described herein. The present invention is also related to treating a disorder responsive to the blockade of sodium channels in a mammal suffering therefrom by administering an effective amount of a compound of Formula VI as described herein.

The present invention is also directed to the use of a compound of Formulae I, VI or IX for the treatment of neuronal damage following global and focal ischemia, for the treatment or prevention of otoneurotoxicity, for the treatment and prevention of eye diseases involving excitatory toxicity, and for the treatment or prevention of neurodegenerative conditions such as amyotrophic lateral sclerosis (ALS), as antimanic depressants, as local anesthetics, as antiarrhythmics and for the treatment or prevention of diabetic neuropathy and for the treatment of pain including chronic pain. The compounds may also be useful for urinary incontinence.

The present invention also is directed to the process for preparing novel substituted semicarbazones and thiosemicarbazones of Formulae I or IX.

A first aspect of the present invention is directed to the use of compounds of Formulae I, VI or IX as blockers of sodium channels.

A second aspect of the present invention is to provide a method for treating, preventing or ameliorating neuronal loss following global and focal ischemia; treating, preventing or ameliorating pain including chronic pain; treating, preventing or ameliorating neurodegenerative conditions, otoneurotoxicity and eye diseases involving glutamate toxicity; treating, preventing or ameliorating manic depression; inducing local anesthesia; and treating arrhythmias by administering a compound of Formulae I, VI or IX to a mammal in need of such treatment.

A number of compounds within the scope of the present invention are novel compounds. Therefore, a third aspect of the present invention is to provide novel compounds of Formulae I or IX, and to also provide for the use of these novel compounds for treating, preventing or ameliorating convulsions.

A fourth aspect of the present invention is to provide a pharmaceutical composition useful for treating disorders responsive to the blockade of sodium ion channels, containing an effective amount of a compound of Formulae I, VI or IX in admixture with one or more pharmaceutically acceptable carriers or diluents.

A fifth aspect of the present invention is directed to methods for preparing novel compounds of Formulae I or IX.

DETAILED DESCRIPTION OF THE INVENTION

Figure 1A:
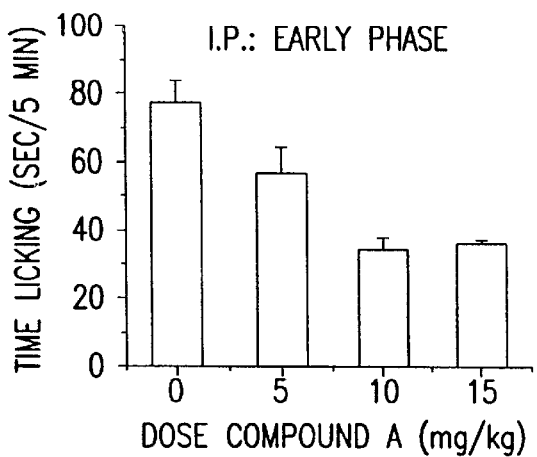
FIGS. 1A and 1B are graphs of the antinociceptive effects (time licking) of a compound of the present invention as a function of i.p. doses of said compound.

The present invention arises out of the discovery that compounds of Formulae I, VI and IX act as blockers of the $Na^+$ channel. In view of this discovery, compounds of Formulae I and IX are useful for treating disorders responsive to the blockade of sodium ion channels.

The compounds useful in this aspect of the present invention are semicarbazones and thiosemicarbazones represented by Formula I:

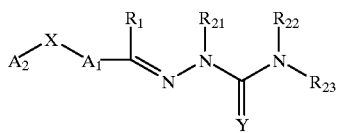

I or a pharmaceutically acceptable salt or prodrug thereof, wherein:

Y is oxygen or sulfur;

$R_1$ is hydrogen, alkyl, cycloalkyl, alkenyl, alkynyl, haloalkyl, aryl, aminoalkyl, hydroxyalkyl, alkoxyalkyl or carboxyalkyl;

$R_{21}$, $R_{22}$ and $R_{23}$ are independently hydrogen, alkyl, cycloalkyl, alkenyl, alkynyl, haloalkyl, aryl, aminoalkyl, hydroxyalkyl, alkoxyalkyl or carboxyalkyl, or $R_{21}$, is defined as above, and $R_{22}$ and $R_{23}$ together with the nitrogen atom to which they are attached form a heterocycle, including piperidine, piperazine, or morpholine;

$A_1$ and $A_2$ are independently aryl, heteroaryl, saturated or partially unsaturated carbocycle or saturated or partially unsaturated heterocycle, any of which is optionally substituted;

X is one or O, S, $NR_{24}$, $CR_{25}R_{26}$, C(O), $NR_{24}C(O)$, $C(O)NR_{24}$, SO, $SO_2$ or a covalent bond; where $R_{24}$ is hydrogen, alkyl, cycloalkyl, alkenyl, alkynyl, haloalkyl, aryl, aminoalkyl, hydroxyalkyl, alkoxyalkyl or carboxyalkyl; and $R_{25}$ and $R_{26}$ are independently hydrogen, alkyl, cycloalkyl, alkenyl, alkynyl, haloalkyl, aryl, aminoalkyl, hydroxyalkyl, alkoxyalkyl or carboxyalkyl.

Preferred compounds falling within the scope of Formula I include compounds wherein $A_1$ and $A_2$ are both aryl moieties, preferably both phenyl moieties, that are each optionally independently substituted by one or two substituents independently selected from the group consisting of halogen, nitro, amino, $C_{1-6}$ alkyl, $C_{3-8}$ cycloalkyl, cyano, $C_{1-6}$ alkoxy or $C_{6-10}$ aryloxy; Y is O; $R_1$ is hydrogen, $C_{1-6}$ alkyl, $C_{3-8}$ cycloalkyl or $C_{6-10}$ aryl; $R_2$, $R_{22}$ and $R_{23}$ are independently hydrogen or $C_{1-6}$ alkyl; and X is oxygen or sulfur.

Preferred compounds within Formula I also include those compounds where $A_1$ is an optionally substituted aryl group selected from the group consisting of phenyl and naphthyl, and $A_2$ is an optionally substituted heteroaryl or aryl group selected from the group consisting of pyridyl, pyrimidinyl, 1,3,5-triazinyl, furanyl, thiophenyl, naphthyl, quinolyl, 3,4-methylenedioxyphenyl, 3,4-ethylenedioxyphenyl, indanyl, tetrahydronaphthyl and quinoxalinyl.

Additional preferred compounds within Formula I also include those compounds where $A_1$ is an optionally substituted aryl group selected from the group consisting of phenyl or naphthyl, and $A_2$ is an optionally substituted carbocycle or heterocycle selected from the group consisting of cyclopentyl, cyclohexyl, cycloheptyl, piperidinyl, morpholinyl, pyrrolidinyl, tetrahydrofuranyl, tetrahydropyranyl, cyclohexenyl, adamantyl, exo-norbornyl and cyclopentenyl.

Additional preferred compounds within Formula I include those compounds where $A_1$ is an optionally substituted heteroaryl or aryl group selected from the group consisting of pyridyl, pyrimidinyl, 1,3,5-triazinyl, naphthyl, quinolyl, furanyl, and thiophenyl, and $A_2$ is an optionally substituted heteroaryl or aryl group selected from the group consisting of phenyl, furanyl, thiophenyl, quinolinyl, 3,4-methylenedioxyphenyl, 3,4-ethylenedioxyphenyl, indanyl, tetrahydronaphthyl and naphthyl.

Additional preferred compounds within Formula I include those compounds where $A_1$ is an optionally substituted, saturated or partially unsaturated carbocycle or heterocycle selected from the group consisting of cyclopentyl, cyclohexyl, cycloheptyl, morpholinyl, piperidinyl, pyrrolidinyl, tetrahydrofuranyl and tetrahydropyranyl, and $A_2$ is an optionally substituted aryl or heteroaryl group selected from the group consisting of phenyl, furanyl, thiophenyl, quinolinyl, 3,4-methylenedioxyphenyl, 3,4-ethylenedioxyphenyl, indanyl, tetrahydronaphthyl, or naphthyl.

Exemplary preferred compounds that may be employed in this method of invention include, without limitation:

4-phenoxybenzaldehyde semicarbazone;
4-(4-fluorophenoxy)benzaldehyde semicarbazone;
4-(4-chlorophenoxy)benzaldehyde semicarbazone;
4-(4-bromophenoxy)benzaldehyde semicarbazone;
4-(4-methoxyphenoxy)benzaldehyde semicarbazone;
4-(4-trifluoromethylphenoxy)benzaldehyde semicarbazone;
4-(4-methylphenoxy)benzaldehyde semicarbazone;
4-(3,4-difluorophenoxy)benzaldehyde semicarbazone;
4-(4-chloro-2-fluorophenoxy)benzaldehyde semicarbazone;
4-(4-nitrophenoxy)benzaldehyde semicarbazone;
4-(3-methylphenoxy)benzaldehyde semicarbazone;
4-(4-t-butylphenoxy)benzaldehyde semicarbazone;
4-(4-propylphenoxy)benzaldehyde semicarbazone;
4-(4-s-butylphenoxy)benzaldehyde semicarbazone;
4-(4-bromophenoxy)acetophenone semicarbazone;
4-(4-fluorophenoxy)acetophenone semicarbazone;
4-(4-chlorophenoxy)acetophenone semicarbazone;
4-(4-bromophenoxy)propiophenone semicarbazone;
4-(4-fluorophenoxy)propiophenone semicarbazone;
4-(4-chlorophenoxy)propiophenone semicarbazone;
4-(2-pyridinoxy)benzaldehyde semicarbazone;
4-(3-pyridinoxy)benzaldehyde semicarbazone;
4-(4-pyridinoxy)benzaldehyde semicarbazone;
4-(2-pyrimidinoxy)benzaldehyde semicarbazone;
4-(4-chloro-2-pyridinoxy)benzaldehyde semicarbazone;
2-phenoxypyridine-5-carboxaldehyde semicarbazone;
2-(4-chlorophenoxy)pyridine-5-carboxaldehyde semicarbazone;
2-(4-fluorophenoxy)pyridine-5-carboxaldehyde semicarbazone;
4-(3,4-methylenedioxyphenoxy)benzaldehyde semicarbazone;
4-phenylmercaptobenzaldehyde semicarbazone;
4-(4-fluorophenylmercapto)benzaldehyde semicarbazone;
4-(4-chlorophenylmercapto)benzaldehyde semicarbazone;
4-cyclohexyloxybenzaldehyde semicarbazone;
4-cycloheptyloxybenzaldehyde semicarbazone;
4-(5-indanyloxy)benzaldehyde semicarbazone;
4-(6-quinolinyloxy)benzaldehyde semicarbazone;
4-(4-fluorophenoxy)-3-fluorobenzaldehyde semicarbazone;
4-(4-fluorophenoxy)cyclohexane-1-carboxaldehyde semicarbazone;
4-(tetrahydropyranyloxy)benzaldehyde semicarbazone;
4-(1-methyl-4-piperidinoxy)benzaldehyde semicarbazone;
4-(4-fluorophenoxy)benzaldehyde 4'-methylsemi carbazone; and
4-(4-fluorophenoxy)benzaldehyde 2'-methylsemicarbazone.

Additionally, compounds of Formula VI can also be employed to block sodium (Na$^+$) channels:

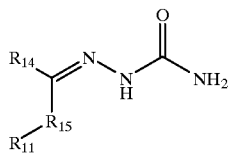

VI or a pharmaceutically effective salt thereof; wherein $R_{11}$ is

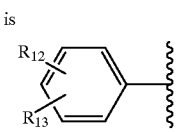

or $R_{11}$, is a 5 to 7 member heterocycle having between 1 and 3 heteroatoms selected from the group consisting of O, S and N, said heterocycle being unsubstituted or substituted with at least one substituent selected from the group consisting of halogen, amino, lower alkylamino, dilower alkylamino, lower alkoxy and aryl, wherein said aryl is unsubstituted or substituted with at least one substituent selected from the group consisting of halogen, amino, lower alkylamino, dilower alkylamino and lower alkoxy;

$R_{12}$ and $R_{13}$ are the same or different and are selected from hydrogen, halogen, lower alkyl, amino, nitro, lower alkoxy, lower alkylidene and lower arylidene, said lower alkyl being unsubstituted or substituted with at least one substituent selected from the group consisting of halogen, amino, lower alkylamino, dilower alkylamino and aryl, wherein said aryl is unsubstituted or substituted with at least one substituent selected from the group consisting of hydrogen, halogen, lower alkyl, lower alkoxy, amino, lower alkylamino and dilower alkylamino, said lower alkoxy, lower alkylidene and lower arylidene being unsubstituted or substituted with at least one substituent selected from the group consisting of halogen, amino, lower alkylamino, dilower alkylamino, lower alkoxy and aryl, wherein said aryl is unsubstituted or substituted with at least one substituent selected from the group consisting of halogen, amino, lower alkylamino, dilower alkylamino and lower alkoxy;

$R_{14}$ is hydrogen, alkyl, alkylidine, haloalkyl, aryl, aminoalkyl, hydroxyalkyl, alkoxyalkyl or carboxyalkyl; and $R_{15}$ is a single bond, an alkyl having between 1 and 10 carbon atoms or an alkylidene having between 2 and 20 carbon atoms, said alkyl being unsubstituted or substituted with at least one substituent selected from the group consisting of halogen, amino, lower alkylamino, dilower alkylamino, lower alkoxy and aryl, wherein said aryl is unsubstituted or substituted with at least one substituent selected from the group consisting of halogen, amino, lower alkylamino, dilower alkylamino and lower alkoxy, said alkylidene being unsubstituted or substituted with at least one substituent selected from the group consisting of halogen, amino, lower alkylamino, dilower alkylamino and aryl, wherein said aryl is unsubstituted or substituted with at least one substituent selected from the group consisting of hydrogen, halogen, lower alkyl, lower alkoxy, amino, lower alkylamino and dilower alkylamino.

Preferred compounds within the scope of Formula VI include those compounds where:

$R_{11}$ is

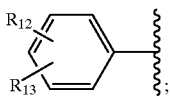

$R_{12}$ and $R_{13}$ are the same or different and are selected from hydrogen, fluorine, chlorine, bromine, iodine, lower alkoxy and lower alkyl;

$R_{14}$ is hydrogen; and $R_{15}$ is a single bond, lower alkyl or a substituted or unsubstituted alkylidene having between 2 and 20 carbon atoms.

Since the compounds of Formula I and VI are blockers of sodium ($Na^+$) channels, a number of diseases and conditions mediated by sodium ion influx can be treated employing these compounds. Therefore, the invention is related to a method of treating, preventing or ameliorating neuronal loss associated with stroke, global and focal ischemia, CNS trauma, hypoglycemia and surgery, spinal cord trauma; as well as treating or ameliorating neurodegenerative diseases including Alzheimer's disease, amyotrophic lateral sclerosis, Parkinson's disease, treating or ameliorating anxiety, convulsions, glaucoma, migraine headache, and muscle spasm. The compounds of Formula I and VI are also useful as antimanic depressants, as local anesthetics, and as antiarrhythmics; as well as for treating, preventing or ameliorating pain including surgical, chronic and neuropathic pain. In each instance, the methods of the present invention require administering to an animal in need of such treatment an effective amount of a sodium channel blocker of the present invention, or a pharmaceutically acceptable salt or prodrug thereof.

The present invention is also directed to novel compounds within the scope of Formula I. These compounds include those compounds of Formula I where:

Y is oxygen or sulfur;

$R_1$, is hydrogen, alkyl, cycloalkyl, alkenyl, alkynyl, haloalkyl, aryl, aminoalkyl, hydroxyalkyl, alkoxyalkyl or carboxyalkyl;

$R_{21}$, $R_{22}$ and $R_{23}$ are independently hydrogen, alkyl, cycloalkyl, alkenyl, alkynyl, haloalkyl, aryl, aminoalkyl, hydroxyalkyl, alkoxyalkyl or carboxyalkyl, or $R_{21}$, is defined as above, and $R_{22}$ and R23 together with the nitrogen atom to which they are attached form a heterocycle, including piperidine, piperazine, morpholine;

$A_1$ and $A_2$ are independently aryl, heteroaryl, saturated or partially unsaturated carbocycle or saturated or partially unsaturated heterocycle, any of which is optionally substituted;

X is one or O, S, $NR_{24}$, $CR_{25}R_{26}$, C(O), $NR_{24}C(O)$, $C(O)NR_{24}$, SO, $SO_2$ or a covalent bond; where $R_{24}$ is hydrogen, alkyl, cycloalkyl, alkenyl, alkynyl, haloalkyl, aryl, aminoalkyl, hydroxyalkyl, alkoxyalkyl or carboxyalkyl; and $R_{25}$ and $R_{26}$ are independently hydrogen, alkyl, cycloalkyl, alkenyl, alkynyl, haloalkyl, aryl, aminoalkyl, hydroxyalkyl, alkoxyalkyl or carboxyalkyl;

provided that:

when X is O or S, $R_2$, $R_{22}$ and $R_{23}$ are hydrogen or alkyl; then $A_1$ and $A_2$ are not both phenyl, optionally substituted by one or two non-hydrogen substituents.

Specifically, preferred substituted semicarbazones and thiosemicarbazones are represented by Formulae II–VI and VIII–IX. In particular, a preferred embodiment is represented by Formulae II and III:

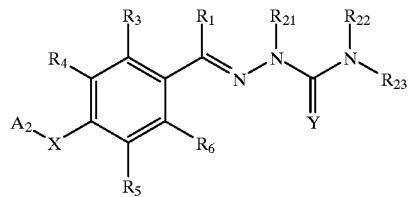

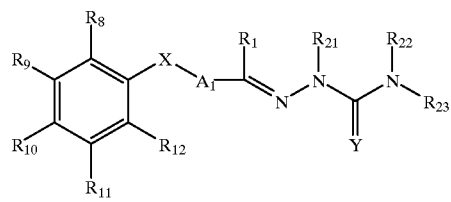

or a pharmaceutically acceptable salt or prodlrug thereof, wherein $R_1$, R21, R22, R23, X, Y. $A_1$ and $A_2$ are as defined previously with respect to Formula I, provided that $A_1$ and $A_2$ are other than optionally substituted phenyl; and $R_3$, $R_4$, $R_5$ and $R_6$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, hetroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamido, hydroxy, thiol, acyloxy, azido, alkoxy, carboxy, carbonylarnido or alkylthiol; or $R_3$ and $R_4$ or $R_5$ and $R_6$ are taken together with the carbon atoms to which they are attached to form a carbocycle or heterocycle. Examples of bridges formed by $R_3$ and $R_4$ or $R_5$ and $R_6$ taken together are —$OCH_2O$—, —$OCF_2O$—, $(CH_2)_3$—, —$(CH_2)_4$—, —$OCH_2CH_2O$—, —$CH_2N(R_7)CH_2$—, —$CH_2CH_2N(R_7)CH_2$—, —$CH_2N(R_7)CH_2CH_2$— and —H=CH—CH=CH—; where $R_7$ is hydrogen, alkyl or cycloalkyl;

$R_8$, $R_9$, $R_{10}$, $R_{11}$ and $R_{12}$ independently are hydrogen, halo, haloalkyl, aryl, cycloalkyl, saturated or partially unsaturated heterocycle, heteroaryl, alkyl, alkenyl, alkynyl, arylalkyl, arylalkenyl, arylalkynyl, heteroarylalkyl, hetroarylalkenyl, heteroarylalkynyl, cycloalkylalkyl, heterocycloalkyl, hvdroxyalkyl, aminoalkyl, carboxyalkyl, alkoxyalkyl, nitro, amino, ureido, cyano, acylamido, hydroxy, thiol, acyloxy, azido, alkoxy, carboxy, carbonylamido or alkylthiol; or one of $R_8$ and $R_9$, or $R_9$ and $R_{10}$, or $R_{10}$ and $R_1$, or $R_{11}$ and $R_{12}$ are taken together with the carbon atoms to which they are attached to form a carbocycle or heterocycle. Examples of bridges formed by $R_8$ and $R_9$, or $R_9$ and $R_{10}$, or $R_{10}$ and $R_{11}$, or $R_{11}$ and $R_{12}$ taken together are —$OCH_2O$—, —$OCF_2O$—, —$(CH_2)_3$—, —$(CH_2)_4$—, —$OCH_2CH_2O$—, —$CH_2N(R_7)CH_2$—, —$CH_2CH_2N(R_7)CH_2O$—, —$CH_2N(R_7)CH_2CH_2$— and —CH=CH—CH=CH—; where $R_7$ is hydrogen, alkyl or cycloalkyl.

Preferred values of $A_2$ in Formula II include furanyl, thiophenyl, quinolinyl, 3,4-methylenedioxyphenyl, 3,4-ethylenedioxyphenyl, indanyl, tetrahydronaphthyl, and naphthyl.

Preferred values of $A_1$ in Formula III include furanyl, thiophenyl, quinolinyl, 3,4-methylenedioxyphenyl, 3,4-ethylenedioxyphenyl, indanyl, tetrahydronaphthyl and naphthyl.

Another preferred embodiment of the invention includes substituted semicarbazones and thiosemicarbazones represented by Formula IV and Formula V:

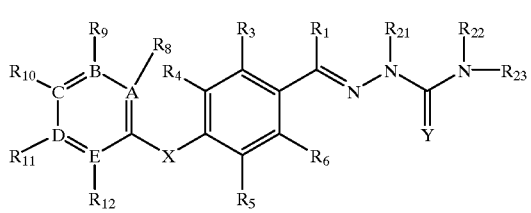

IV

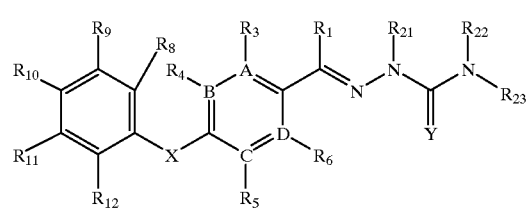

V or a pharmaceutically acceptable salt or prodrug thereof, wherein $R_1$, $R_3$–$R_6$, $R_8$–$R_{12}$, Y and X are as defined previously with respect to Formulae I, II and III; and A, B, C, D and E are independently nitrogen or carbon, provided that no more than three of A, B, C, D and E are nitrogen, and there is no substituent, except for oxygen (when the nitrogen is present as a N-oxide), present on A, B, C, D or E when said A, B, C, D or E represents nitrogen.

Preferred compounds of Formula IV are those where one, two or three of A through E are nitrogens. Preferred compounds of Formula V are those where one or two of A through D are nitrogens.

Another preferred embodiment of the invention includes substituted semicarbazones and thiosemicarbazones represented by Formula VII and Formula VIII:

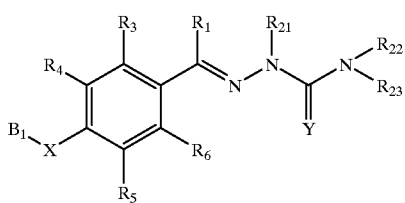

VII

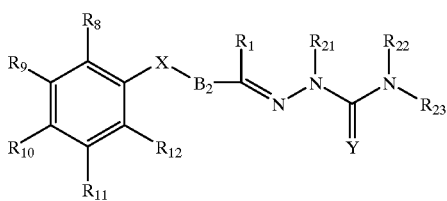

VIII or a pharmaceutically acceptable salt or prodrug thereof, wherein $R_1$, $R_3$–$R_6$, $R_8$–$R_{12}$, Y and X are as defined previously with respect to Formula I through III;

$B_1$, is an optionally substituted, saturated or partially unsaturated carbocycle or optionally substituted, saturated or partially unsaturated heterocycle; and $B_2$ is an optionally substituted, saturated or partially unsaturated carbocycle or optionally substituted, saturated or partially unsaturated heterocycle.

Preferred $B_1$ and $B_2$ independently include cyclopentyl, cyclohexyl, cycloheptyl, tetrahydrofuranyl, tetrahydropyranyl, pyrrolidinyl or piperidinyl.

Another preferred embodiment of the invention includes substituted semicarbazones and thiosemicarbazones represented by Formula IX:

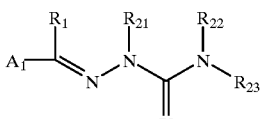

IX or a pharmaceutically acceptable salt or prodrug thereof, wherein $R_1$, $R_{21}$–$R_{23}$, Y and $A_1$ are as defined previously with respect to Formula I. Novel compounds of Formula IX are those wherein a) one of $R_{21}$–$R_{23}$ is other than hydrogen; or b) $A_1$ is optionally substituted, saturated or partially unsaturated carbocycle or optionally substituted, saturated or partially unsaturated heterocycle; or c) when $A_1$ is phenyl, $A_1$ is substituted by more than two substituents which are other than hydrogen; or d) $A_1$ is a bicyclic aryl.

Another preferred embodiment of the invention includes substituted semicarbazones and thiosemicarbazones represented by Formula X:

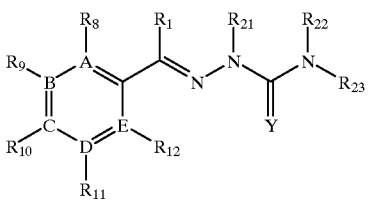

X or a pharmaceutically acceptable salt or prodrug thereof, wherein $R_1$, $R_{21}$–$R_{23}$, Y, A, B, C, D, E, and $R_8$–$R_{12}$ are as defined previously with respect to Formulae I and IV. Novel compounds of Formula X are those compounds wherein a) one of $R_{21}$–$R_{23}$ is other than hydrogen; or b) more than two of $R_8$–$R_{12}$ are other than hydrogen; or c) one of $R_8$ and $R_9$, or $R_9$ and $R_{10}$, or $R_{10}$ and $R_{11}$, or $R_{11}$, and $R_{12}$ are taken together with the carbon atoms to which they are attached to form a carbocycle or heterocycle. Examples of bridges formed by $R_8$ and $R_9$, or $R_9$ and $R_{10}$, or $R_{10}$ and $R_{11}$, or $R_{11}$, and $R_{12}$ taken together are —$OCH_2O$—, —$OCF_2O$—, $(CH_2)_3$—, —$(CH_2)_4$—, —$OCH_2CH_2O$—, —$CH_2N(R_7)$$CH_2$—, —$CH_2CH_2N(R_7)CH_2$—, —$CH_2N(R_7)CH_2CH_2$—, and —CH═CH—CH═CH—; where $R_7$ is hydrogen, alkyl or cycloalkyl.

Generally, preferred compounds of Formulae I–V and VII–X are those compounds where $R_1$ is hydrogen or alkyl, more preferably hydrogen, methyl or ethyl, and where $R_{21}$, $R_{22}$ and $R_{23}$ are independently hydrogen or $C_{1-4}$ alkyl.

Preferred values of X in Formulae I–V and VII–X are O and S. A preferred value of Y in Formulae I–V and VII–X is O.

Preferred values of $R_3$, $R_4$, $R_5$, $R_6$, and $R_8$–$R_{12}$, with respect to Formulae II–V and VII–X include hydrogen, halo, $C_1$–$C_6$ haloalkyl, $C_6$–$C_{10}$ aryl, $C_4$–$C_7$ cycloalkyl, $C_1$–$C_6$ alkyl, $C_2$–$C_6$ alkenyl, $C_2$–$C_6$ alkynyl, $C_6$–$C_{10}$ aryl($C_1$–$C_6$) alkyl, $C_6$–$C_{10}$aryl($C_2$–$C_6$) alkenyl, $C_6$–$C_{10}$ aryl($C_2$–$C_6$) alkynyl, $C_1$–$C_6$ hydroxyalkyl, nitro, amino, ureido, cyano, $C_1$–$C_6$ acylamido, hydroxy, thiol, $C_1$–$C_6$ acyloxy, azido, $C_1$–$C_6$ alkoxy, or carboxy. Alternatively, $R_3$ and $R_4$ or $R_5$ and $R_6$, or two adjacent $R_8$ through $R_{12}$ can form a bridge selected from the group consisting of —OCH$_2$O—, —(CH$_2$)$_3$—, —(CH$_2$)$_4$—, —OCH$_2$CH$_2$O—, —CH$_2$N(R$_7$)CH$_2$—, —CH$_2$CH$_2$N(R$_7$) CH$_2$—, —CH$_2$N(R$_7$)CH$_2$CH$_2$—, and —CH═CH—CH═CH—, where $R_7$ is hydrogen or $C_1$–$C_6$ alkyl. Most preferably, at least one, two or three of $R_3$, R4, $R_5$, $R_6$ are hydrogen. Most preferably, at least one, two or three of $R_8$ through $R_{12}$ are hydrogen.

With respect to the novel methods of treatment of the present invention, an additional preferred subset of substituted semicarbazone compounds includes compounds of Formula I, wherein $A_1$ and $A_2$ are phenyl moieties, that are each independently substituted by one or two substituents independently selected from the group consisting of halogen, $C_{1-6}$ alkyl, $C_{3-8}$ cycloalkyl, cyano, $C_{1-6}$ alkoxy or $C_{6-10}$ aryloxy; $R_1$ is hydrogen, $C_{1-6}$ alkyl, $C_{3-8}$ cycloalkyl or $C_{6-10}$ aryl; Y is oxygen and X is oxygen or sulfur.

Useful compounds in this aspect of the present invention include:

4-phenoxybenzaldehyde semicarbazone;
4-(4-fluorophenoxy)benzaldehyde semicarbazone;
4-(4-chlorophenoxy)benzaldehyde semicarbazone;
4-(4-bromophenoxy)benzaldehyde semicarbazone;
4-(4-methoxyphenoxy)benzaldehyde semicarbazone;
4-(4-trifluoromethylphenoxy)benzaldehyde semicarbazone;
4-(4-methylphenoxy)benzaldehyde semicarbazone;
4-(3,4-difluorophenoxy)benzaldehyde semicarbazone;
4-(4-chloro-2-fluorophenoxy)benzaldehyde semicarbazone;
4-(4-nitrophenoxy)benzaldehyde semicarbazone;
4-(3-methylphenoxy)benzaldehyde semicarbazone;
4-(4-t-butylphenoxy)benzaldehyde semicarbazone;
4-(4-propylphenoxy)benzaldehyde semicarbazone;
4-(4-s-butylphenoxy)benzaldehyde semicarbazone;
4-(4-bromophenoxy)acetophenone semicarbazone;
4-(4-fluorophenoxy)acetophenone semicarbazone;
4-(4-chlorophenoxy)acetophenone semicarbazone;
4-(4-bromophenoxy)propiophenone semicarbazone;
4-(4-fluorophenoxy)propiophenone semicarbazone;
4-(4-chlorophenoxy)propiophenone semicarbazone;
4-phenylmercaptobenzaldehyde semicarbazone;
4-(4-fluorophenylmercapto)benzaldehyde semicarbazone;
4-(4-chlorophenylmercapto)benzaldehyde semicarbazone;
4-cyclohexyloxybenzaldehyde semicarbazone;
4-cycloheptyloxybenzaldehyde semicarbazone;
4-(5-indanyloxy)benzaldehyde semicarbazone;
4-(6-quinolinyloxy)benzaldehyde semicarbazone;
4-(4-fluorophenoxy)-3-fluorobenzaldehyde semicarbazone;
4-(4-fluorophenoxy)cyclohexane-1-carboxaldehyde semicarbazone;
4-(tetrahydropyranyloxy)benzaldehyde semicarbazone;
4-(1-methyl-4-piperidinoxy)benzaldehyde semicarbazone;
4-(4-fluorophenoxy)benzaldehyde4'-methylsemicarbazone; and
4-(4-fluorophenoxy)benzaldehyde2'-methylsemicarbazone.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl and cyclohexyl and cycloheptyl.

Useful saturated or partially saturated carbocyclic groups are cycloalkyl groups as defined above, as well as cycloalkenyl groups, such as cyclopentenyl, cycloheptenyl and cyclooctenyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups are $C_{2-6}$ alkenyl groups, preferably $C_{2-4}$ alkenyl. Typical $C_{2-4}$ alkenyl groups include ethenyl, propenyl, isopropenyl, butenyl, and sec.-butenyl.

Useful alkynyl groups are $C_{2-6}$ alkynyl groups, preferably $C_{2-4}$ alkynyl. Typical $C_{2-4}$ alkynyl groups include ethynyl, propynyl, butynyl, and 2-butynyl groups.

Useful arylalkyl groups include any of the abovementioned $C_{1-10}$ alkyl groups substituted by any of the abovementioned $C_{6-14}$ aryl groups. Useful values include benzyl, phenethyl and naphthylmethyl.

Useful arylalkenyl groups include any of the abovementioned $C_{2-4}$ alkenyl groups substituted by any of the abovementioned $C_{6-14}$ aryl groups.

Useful arylalkynyl groups include any of the abovementioned $C_{2-4}$ alkynyl groups substituted by any of the abovementioned $C_{6-14}$ aryl groups. Useful values include phenylethynyl and phenylpropynyl.

Useful cycloalkylalkyl groups include any of the abovementioned $C_{1-10}$ alkyl groups substituted by any of the abovementioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulphur substituted by one of the $C_{1-10}$ alkyl groups mentioned above.

Useful acylamino groups are any $C_{1-6}$ acyl (alkanoyl) attached to an amino nitrogen, e.g. acetamido, propionamido, butanoylamido, pentanoylamido, hexanoylamido as well as arylsubstituted $C_{2-6}$ substituted acyl groups.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

Useful saturated or partially saturated heterocyclic groups include tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl and pyrazolinyl groups.

Useful heterocycloalkyl groups include any of the abovementioned $C_{1-10}$ alkyl groups substituted by any of the abovementioned heterocyclic groups.

Useful heteroaryl groups include any one of the following: thienyl, benzo[b]thienyl, naphtho[2,3-b]thienyl, thianthrenyl, furyl, pyranyl, isobenzofliranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, 5aH-carbazolyl, carbazolyl, (carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, 4-nitrobenzofurazan, benzimidazolyl, 2-oxindolyl and 2-oxobenzimidazolyl. Where the heteroaryl group contains a nitrogen atom in a ring, such nitrogen atom may be in the form of an N-oxide, e.g. a pyridyl N-oxide, pyrazinyl N-oxide, pyrimidinyl N-oxide and the like.

Useful heteroarylalkyl groups include any of the abovementioned $C_{1-10}$ alkyl groups substituted by any of the above-mentioned heteroaryl groups.

Useful heteroarylalkenyl groups include any of the abovementioned $C_{2-4}$ alkenyl groups substituted by any of the above-mentioned heteroaryl groups.

Useful heteroarylalkynyl groups include any of the abovementioned $C_{2-4}$ alkynyl groups substituted by any of the above-mentioned heteroaryl groups.

Useful amino groups include —$NH_2$, —$NHR_{14}$, and —$NR_{14}R_{15}$, wherein $R_{14}$ and $R_{15}$ are $C_{1-10}$ alkyl or cycloalkyl groups as defined above.

Useful aminocarbonyl groups are carbonyl groups substituted by —$NH_2$, —$NHR_{14}$, and —$NR_{14}R_{15}$, wherein $R_{14}$ and $R_{15}$ are $C_{1-10}$ alkyl groups.

Optional substituents on any of the aryl, heterocyclic, heteroaryl, and cycloalkyl rings in Formulae I–V include any one of halo, haloalkyl, aryl, heterocycle, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, hydroxy, thiol, acyloxy, azido, alkoxy, carboxy, aminocarbonyl, and alkylthiol groups mentioned above. Preferred optional substituents include: halo, haloalkyl, hydroxyalkyl, aminoalkyl, nitro, alkyl, alkoxy and amino.

The term "lower" as employed herein refers to a group having up to four carbon atoms. Saturated groups can have 1 to 4 carbon atoms. Unsaturated groups can have 2 to 4 carbon atoms.

Additional exemplary preferred compounds of Formula I include, without limitation:

4-(3,4-methylenedioxyphenoxy)benzaldehyde semicarbazone;
4-(2-pyridinoxy)benaldehyde semicarbazone;
4-(3-pyridinoxy)benzaldehyde semicarbazone;
4-(4-pyridinoxy)benzaldehyde semicarbazone;
4-(4-chloro-2-pyridinoxy)benzaldehyde semicarbazone;
2-phenoxypyridine-5-carboxaldehyde semicarbazone;
2-(4-chlorophenoxy)pyridine-5-carboxaldehyde semicarbazone;
2-(4-fluorophenoxy)pyridine-3-carboxaldehyde semicarbazone;
4-(2-pyrimidinoxy)benzaldehyde semicarbazone;
4-cyclohexyloxybenzaldehyde semicarbazone;
4-cycloheptyloxybenzaldehyde semicarbazone;
4-(5-indanyloxy)benzaldehyde semicarbazone;
4-(6-quinolinyloxy)benzaldehyde semicarbazone;
4-(4-fluorophenoxy)-3-fluorobenzaldehyde semicarbazone;
4-(4-fluorophenoxy)cyclohexane-1-carboxaldehyde semicarbazone;
4-(tetrahydropyranyloxy)benzaldehyde semicarbazone;
4-(1-methyl-4-piperidinoxy)benzaldehyde semicarbazone;
4-(4-fluorophenoxy)benzaldehyde 4'-methylsemicarbazone;
4-(4-fluorophenoxy)benzaldehyde 2'-methylsemicarbazone; and compounds set forth in the Examples, but not listed here.

Certain of the compounds of Formula I may exist as E, Z-stereoisomers about the C=N double bond and the invention includes the mixture of isomers as well as the individual isomers that may be separated according to methods that are well known to those of ordinary skill in the art. Certain of the compounds of the present invention may exist as optical isomers and the invention includes both the racemic mixtures of such optical isomers as well as the individual entantiomers that may be separated according to methods that are well know to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate, acetic acid, dichloroacetic acid and oxalate.

Examples of prodrugs include esters or amides of Formula I with $R_3$–$R_6$ as hydroxyalkyl or aminoalkyl, and these may be prepared by reacting such compounds with anhydrides such as succinic anhydride.

The invention is also directed to a method for treating disorders responsive to the blockade of sodium channels in animals suffering thereof. Particular preferred embodiments of the substituted semicarbazones for use in method of this invention are represented by previously defined Formula I.

The compounds of this invention may be prepared using methods known to those skilled in the art, or by the novel methods of this invention. The methods described in PCT published application WO96/40628, can be employed to synthesize compounds within the scope of the invention.

Compounds with Formulae I–III can be prepared as illustrated by exemplary reactions in Scheme 1.

Scheme 1

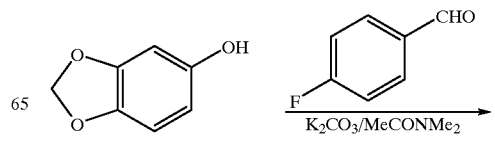

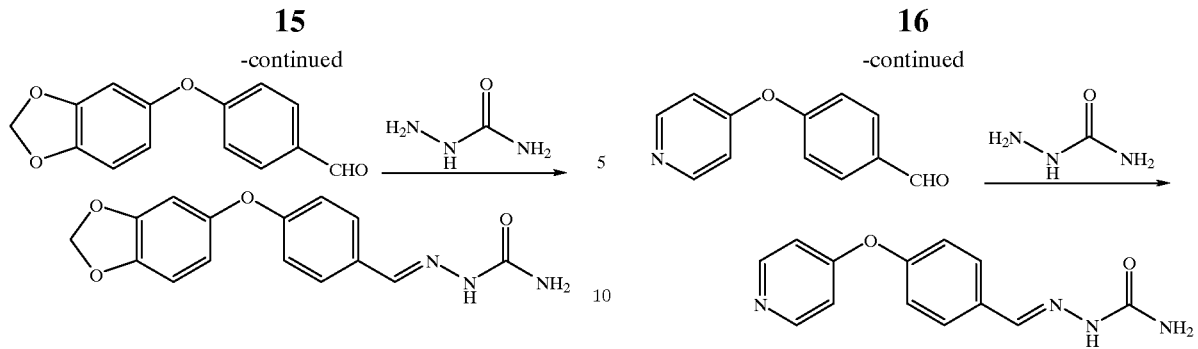

Compounds with Formulae I–II and IV can be prepared as illustrated by exemplary reactions in Scheme 2.

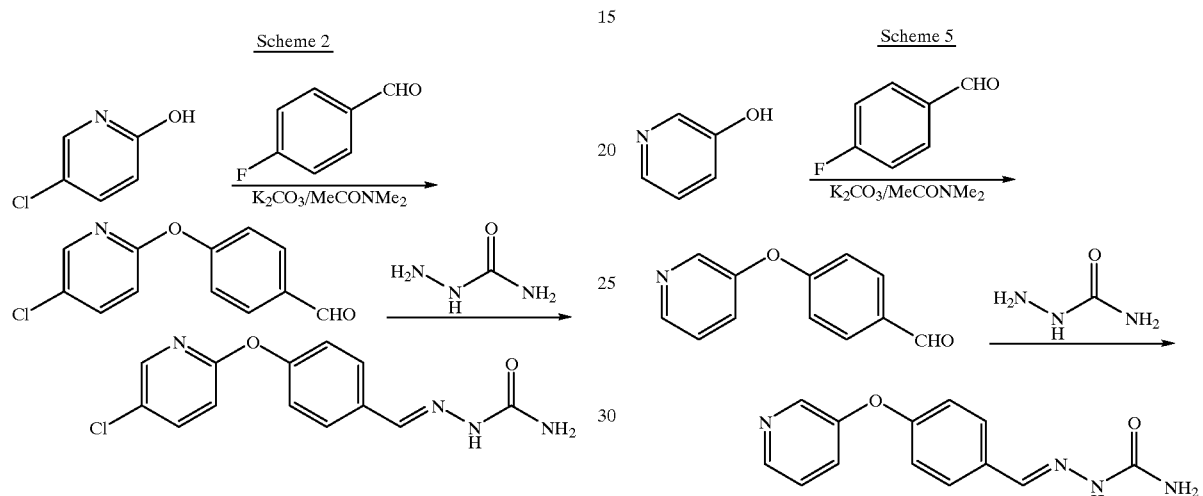

Alternatively, compounds with Formulae I–II and IV can be prepared as illustrated by exemplary reactions in Scheme 3.

Compounds with Formulae I–II and IV also can be prepared as illustrated by exemplary reactions in Schemes 4 and 5.

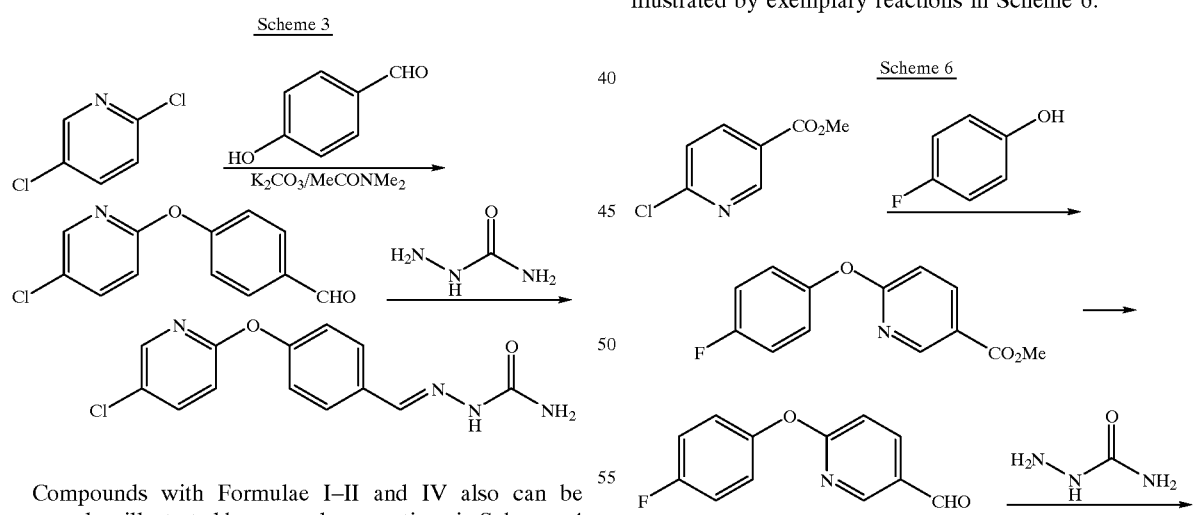

Compounds with Formulae I, III and V can be prepared as illustrated by exemplary reactions in Scheme 6.

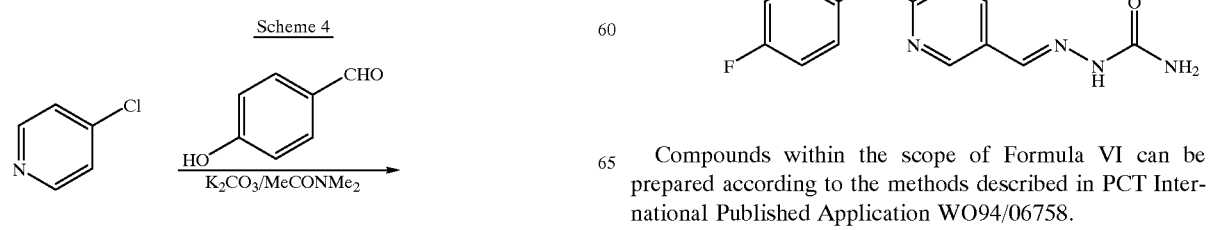

Compounds within the scope of Formula VI can be prepared according to the methods described in PCT International Published Application WO94/06758.

Compounds with Formula VIII can be prepared as illustrated by exemplary reactions in Scheme 7.

Scheme 7

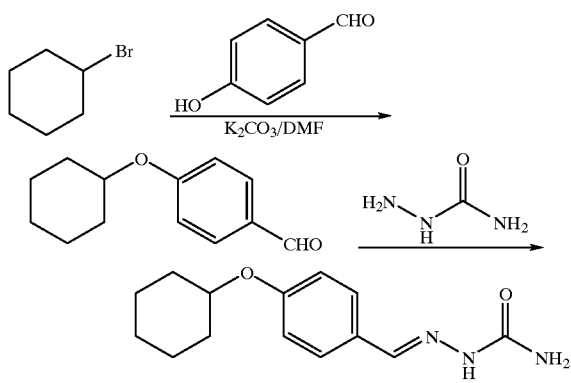

Compounds with Formula IX can be prepared as illustrated by exemplary reactions in Scheme 8.

Scheme 8

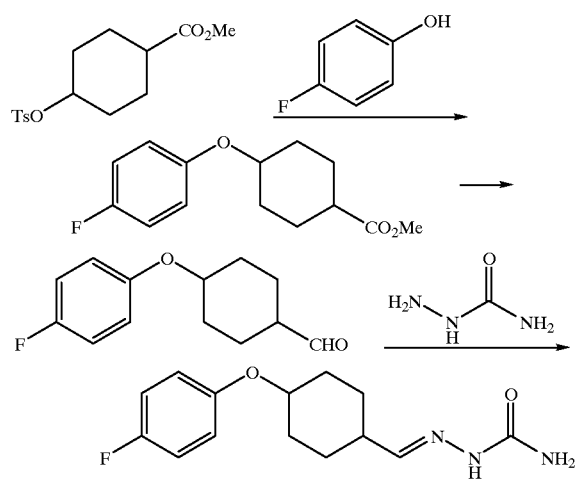

The compounds of the present invention were assessed by electrophysiological assays in dissociated hippocampal neurons for sodium channel blocker activity. These compounds also could be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of $Na^+$ permeability in response to depolarization associated with the action potential in many excitable cells including muscle, nerve and cardiac cells.

One aspect of the present invention is the discovery of the mechanism of action of the compounds herein described as specific $Na^+$ channel blockers. In one aspect of the present invention it has been discovered that compounds disclosed in International published applications WO 94/06758 and WO 96/40628 are specific $Na^+$ channel blockers. Based upon the discovery of this mechanism, these compounds, as well as novel compounds described herein, are contemplated to be useful in treating or preventing neuronal loss due to focal or global ischemia, and in treating or preventing neurodegenerative disorders including ALS, anxiety, and epilepsy. They are also useful in treating or preventing otoneurotoxicity including acute and progressive hearing loss and tinnitus. They are also expected to be effective in treating, preventing or ameliorating neuropathic pain, surgical pain and chronic pain. The compounds are also expected to be useful as antiarrhythmics, anesthetics and antimanic depressants.

The present invention is directed to compounds of Formulae I and VI that are blockers of voltage-sensitive sodium channels. According to the present invention, those compounds having preferred sodium channel blocking properties exhibit an $IC_{50}$ of about 100 µM or less in the electrophysiological assay described herein. Preferably, the compounds of the present invention exhibit an $IC_{50}$ of 10 µM or less. Most preferably, the compounds of the present invention exhibit an $IC_{50}$ of about 1.0 µM or less. Substituted semicarbazones disclosed in WO 94/06758 and WO 96/40628, as well as novel compounds of the present invention, may be tested for their $Na^+$ channel blocking activity by the following electrophysiological and binding assays.

Electrophysiological Assay

Cell preparation

Acute cultures of rat hippocampal neurons were prepared daily using a modification of procedures described previously (Kuo and Bean, Mol. Pharm. 46:716–725 (1994)). Briefly, hippocampi were isolated from 3–11 day old rat pup brains (Sprague-Dawley; Charles River) and were sectioned, by hand, into 0.5–1 mm thick transverse slices (Whittemore and Koerner, Eur. J. Pharm. 192:435–438 (1991)). Slices were incubated for at least 30 min at room temperature (20–24° C.) in an oxygenated medium (124 mM NaCl, 3.3 mM KCl, 2.4 mM $MgSO_4$, 2.5 mM $CaCl_2$, 1.2 mM $KH_2PO_4$, 26 mM $NaHCO_3$, pH=7.4) continuously bubbled with 5% $CO_2$/95% $O_2$. Prior to recording, 4–5 slices were transferred to an oxygenated dissociation medium (82 mM $NaSO_4$, 30 mM $K_2SO_4$, 3 mM $MgCl_2$, 2 mM HEPES, 26 mM $NaHCO_3$, 0.001% phenol red, pH=7.4) containing 3 mg/mL protease XXIII (Sigma, St. Louis, Mo.) and incubated for 10–15 min at 37° C., while continuously bubbling with 5% $CO_2$ / 95% $O_2$. Enzymatic digestion was terminated by transferring the slices to dissociation medium without bicarbonate, supplemented with 1 mg/mL bovine serum albumin and 1 mg/mL trypsin inhibitor (Sigma, St. Louis, Mo.). Slices were then transferred to a 35 mm culture dish containing dissociation medium without bicarbonate, and triturized with a fire-polished glass Pasteur pipette to release single cells. Cells were allowed to settle in this dish for ~30 minutes and were then used for making electrical recordings.

Patch-clamp recordings of voltage-sensitive $Na^+$ currents

Whole-cell voltage-clamp recordings were made using conventional patch-clamp technique (Hamill et al., Pfluegers Arch. 391:85–100 (1981)) with an Axopatch 200 A amplifier (Axon Instruments, Foster City, Calif.). Recordings were made within 2–3 hours after neuron dissociation. The recording chamber was continuously superfused with Tyrode's solution (156 mM NaCl, 3.5 M KCl, 2 mM $CaCl_2$, 5 mM $NaHCO_3$, 10 mM HEPES, 10 mM glucose, pH 7.4) at a speed of about 1 ml/min. Thin-walled pipettes were pulled from 100µl Clay Adams Accu-Fill 90 Micropet disposable pipettes (Becton, Dickenson and Company, Parsipanny, N.J.), fire-polished and sylgarded (Dow-Coming, Midland, Mich.). The pipette resistances ranged from 1 to 3 MΩ when the pipettes were filled with internal solution containing (in mM): 130 CsF, 20 NaCl, 1 $CaCl_2$, 2 $MgCl_2$, 10 EGTA, 10 HEPES, pH adjusted to 7.4 with CsOH. Drugs and intervening wash-outs were applied through a linear array of flow pipes (Drummond Microcaps, 2-µl, 64-mm length). Compounds are dissolved in dimethylsulfoxide (DMSO) to make a 10 mM stock solution, which was subsequently diluted into Tyrode's solution to give final concentrations of 0.1–20 µM. At the highest (1%) concentration, DMSO inhibited the size of $Na^+$ current only slightly. Currents were recorded at room temperature (22–25° C.), filtered at 5 kHz with 4-pole Bessel filter, digitized at 20–50-µs intervals, and stored using Digidata 1200 analog/digital interface with Pclamp6/Clampex software (Axon Instruments). Residual series resistance ranged from 0.4 to 0.8 MΩ after partial compensation (typically ~90%). The inhibitory potency of drugs was assessed by measuring reductions in the peak amplitude of $Na^+$ currents induced by increasing concentrations of compounds tested. $Na^+$ currents were elicited by stepping membrane voltage from holding potentials over the range –100 mV to –50 mV, to a pulse potential of –10 mV. The test pulse duration was 5–10 msec, repeated at a frequency $\leq 1$ Hz. Concentration-inhibition curves were fitted with equation 1:

$$I/I_{control}=1/(1+([compound]/IC_{50})) \qquad \text{Eq. 1}$$

where $I_{control}$ is the maximal $Na^+$ current in the absence of antagonist, [compound] is the drug concentration, and $IC_{50}$ is the concentration of compound that produces half maximal inhibition.

Binding Assay

The ability of compounds of the present invention to modulate either site 1 or site 2 of the $Na^+$ channel was determined following the procedures fully described in Yasushi, *J. Biol. Chem.* 261:6149–6152 (1986) and Creveling, *Mol. Pharmacol.* 23:350–358 (1983), respectively. Rat forebrain membranes were used as sources of $Na^+$ channel proteins. The binding assays were conducted in 130 (M choline chloride at 37(C for 60-minute incubation with [$^3$H] saxitoxin and [$^3$H] batrachotoxin as radioligands for site 1 and site 2, respectively.

The compounds of the present invention may be tested for in vivo anticonvulsant activity after iv or ip injection using a number of anticonvulsant tests in mice (audiogenic seizure model in DBA-2 mice, pentylenetetrazol-induced seizures in mice, maximum electroshock seizure test (MES)).

The compounds may be tested for their neuroprotective activity after focal and global ischemia produced in rats or gerbils according to the procedures described in Buchan et al. (*Stroke*, Suppl. 148–152 (1993)) and Sheardown et al. (*Eur. J. Pharmacol.* 236:347–353 (1993)) and Graham et al. (*J. Pharmacol. Exp. Therap.* 276:1–4 (1996)).

The compounds may be tested for their neuroprotective activity after traumatic spinal cord injury according to the procedures described in Wrathall et. al. (*Exp. Neurology* 137:119–126 (1996)) and Iwasaki et. aL (*J. Neuro Sci.* 134:21–25 (1995)).

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular semicarbazones of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the particular semicarbazones of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal which may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

4-(4-Chloro-2-pyridinoxy)benzaldelhyde semicarbazone a) 4-(4-Chloro-2-pyridinoxy)benzaldehyde To a solution of 4-fluorobenzaldehyde (3.6 g, 29 mmol) in N,N-dimethylacetamide (25 mL) was added 5-chloro-2-pyridinol (4.1 g, 32 mmol) and $K_2CO_3$ (4.1 g, 30 mmol) at room temperature under argon. The mixture was heated to reflux for 4 h, cooled to room temperature, diluted with ethyl acetate (150 mL), washed with water and brine, dried over $Na_2SO_4$, and concentrated in vacuo. The residue was purified by chromatography to yield the title compound as a white solid (0.59 g, 2.5 mmol, 8%). $^1H$ NMR ($CDCl_3$): δ 9.99 (s, 1H), 8.16 (s, 1H), 7.94 (d, J=7.7, 2H), 7.27 (d, J=7.7, 2H), 7.71 (d, J=8.6, 1H), 6.99 (d, J=8.6, 1H).

b) 4-(4-Chloro-2-pyridinoxy)benzaldehyde semicarbazone

To a solution of 4-(4-chloro-2-pyridinoxy)benzaldehyde (330 mg, 1.41 mmol) in ethanol (10 mL) was added a solution of semicarbazide hydrochloride (213 mg, 1.84 mmol) and sodium acetate trihydrate (224 mg, 1.65 mmol) in water (5 mL). The mixture was stirred at room temperature for 30 min., and the resulting solid was collected by filtration, washed with water and dried in vacuo to yield the title compound as a white solid (400 mg, 1.36 mmol, 96%), mp: 231–233° C. $^1H$ NMR (DMSO-$d_6$): δ 10.22 (s, 1H), 8.22 (d, J=2.5, 1H), 7.97 (dd, J=2.5, 8.7, 1H), 7.85 (s, 1H), 7.77 (d, J=8.7, 2H), 7.15 (d, J=8.7, 2H) 7.12 (d, J=8.7, 1H), 6.47 (s, 2H).

EXAMPLE 2

4-(4-Pyridinoxy)benzaldehyde semicarbazone a) 4-(4-Pyridinoxy)benzaldehyde:

To a solution of 4-hydroxybenzaldehyde (2.8 g, 23 mmol) in N,N-dimethylacetamide (30 mL) was added 4-chloropyridine hydrochloride (3.4 g, 23 mmol) and $K_2CO_3$ (5.0 g, 36 mmol) at room temperature under argon. The mixture was heated to reflux for 6 h, cooled to room temperature, diluted with ethyl acetate (75 mL), washed with water, 2N NaOH and brine, dried over $Na_2SO_4$, and concentrated in vacuo. The residue was purified by chromatography to yield the title compound as a colorless liquid (0.57 g, 2.9 mmol, 13%). $^1H$ NMR ($CDCl_3$): δ 10.00 (s, 1H), 8.56 (d, J=6.0, 2H), 7.96 (d, J=8.5, 2H), 7.23 (d, J=8.5, 2H), 6.93 (d, J=6.0, 2H).

b) 4-(4-Pyridinoxy)benzaldehyde semicarbazone:

To a solution of 4-(4-pyridinoxy)benzaldehyde (570 mg, 2.86 mmol) in ethanol (10 mL) was added a solution of semicarbazide hydrochloride (350 mg, 3.03 mmol) and sodium acetate (235 mg, 2.86 mmol) in water (5 mL). The mixture was stirred at room temperature for 30 min., diluted with ethyl acetate (75 mL), washed with 2N NaOH, water and brine, dried over $Na_2SO_4$, concentrated in vacuo to yield the title compound as a white solid (720 mg, 2.77 mmol, 97%), mp: 212–213° C. $^1H$ NMR (DMSO-$d_6$): δ 10.29 (s, 1H), 8.49 (d, J=4.9, 2H), 7.87 (s, 1H), 7.84 (d, J=8.5, 2H), 7.19 (d, J=8.5, 2H), 6.96 (d, J=4.9, 2H), 6.53 (s, 2H).

4-(2-Pyridinoxy)benzaldehyde semicarbazone is prepared as described for 4-(4-pyridinoxy)benzaldehyde semicarbazone.

2-Phenoxypyridine-5-carboxaldehyde semicarbazone, 2-(4-chlorophenoxy)pyridine-5-carboxaldehyde semicarbazone and 2-(4-fluorophenoxy)pyridine-3-carboxaldehyde semicarbazone are prepared from the corresponding aldehydes as described for 4-(5-indanoxy)benzaldehyde semicarbazone.

EXAMPLE 3

4-(3-Pyridinoxy)benzaldehyde semicarbazone a) 4-(3-pyridinoxy)benzaldehyde:

A mixture of 4.02 g (42.3 mmol) of 3-hydroxypyridine, 5.40 g (43.5 mmol) of 4-fluorobenzaldehyde and 5.92 g (42.8 mmol) of anhydrous potassium carbonate in dimethylacetarnide (40 mL) was refluxed (~180° C.) overnight. It was cooled to room temperature, and poured into water (50 mL). The mixture was extracted with 1:1 hexane/ethyl acetate (2×50 mL). The combined extract was washed with water (50 mL), 0.4 N NaOH (50 mL) and water (50 mL), dried ($NaSO_4$) and evaporated to leave 7.62 g of oil, which was used for the next reaction.

b) 4-(3-Pyridinoxy)benzaldehyde semicarbazone:

To a solution of 659 mg (3.31 mmol) of the oil in absolute ethanol (10 mL) was added dropwise a solution of 369 mg (3.31 mmol) of semicarbazide hydrochloride and 274 mg (3.31 mmol) of sodium acetate in water (3 mL). The solution was stirred at room temperature for 2 h to give white precipitates. The mixture was filtered and the solid was washed with methanol (1 mL), dried to leave 320 mg (37%) of the title compound as white solid. More solid was observed in the filtrate. It was filtered and washed by water (2 mL), dried to leave 302 mg (35%) of the title compound as white solid, mp 160–162° C. $^1$H NMR (DMSO-$d_6$): δ 10.23 (s, 1H), 8.39 (m, 2H), 7.82 (s, 1H), 7.76 (d, J=8.4, 2H), 7.47 (m, 2H), 7.05 (d, J=8.4, 2H), 6.48 (s, 2H).

EXAMPLE 4

4-(3,4-methylenedioxyphenoxy)benzaldehyde semicarbazone a) 4-(3,4-methylenedioxyphenoxy)benzaldehyde:

To a solution of 4-fluorobenzaldehyde (1.9 g, 15 mrnmol) in N,N-dimethylacetamide (25 mL) was added sesamol (2.1 g, 15 mrol) and $K_2CO_3$ (2.2 g, 16 mmol) at room temperature under argon. The mixture was heated to reflux for 5 h, cooled to room temperature, diluted with ethyl acetate (100 mL), washed with water and brine, dried over $Na_2SO_4$ and concentrated in vacuo. The residue was purified by chromatography to yield the title compound as a white solid (1.7 g, 7.0 mmol, 46%). $^1$H NMR (CDCl$_3$): δ 9.91 (s, 1H), 7.84 (d, J=8.8, 2H), 7.03 (d, J=8.8, 2H), 6.82 (d, J=8.3, 1H), 6.62 (d, J=2.3, 1H), 6.56 (dd, J=2.3, 8.3, 1H), 6.02 (s, 2H).

b) 4-(3,4-methylenedioxyphenoxy)benzaldehyde semicarbazone:

To a solution of 4-(3,4-methylenedioxyphenoxy) benzaldehyde (1.7 g, 7.0 mmol) in ethanol (40 mL) was added a solution of semicarbazide hydrochloride (0.82 g, 7.1 mmol) and sodium acetate (0.55 g, 6.7 mmol) in water (10 mL). The mixture was stirred at room temperature for 30 min. The resulting white solid was collected by filtration, washed with water and dried in vacuo to yield the title compound (1.2 g, 4.0 mmol, 57%), mp: 225–226° C. $^1$H NMR (DMSO-$d_6$): δ 10.17 (s, 1H), 7.80 (s, 1H), 7.70 (d, J=8.7, 2H), 6.93 (d, J=8.3, 1H), 6.92 (d, J=8.7, 2H), 6.77 (d, J=2.4, 1H), 6.53 (dd, J=2.4, 8.3, 1H), 6.44 (s, 2H), 6.06 (s, 2H).

EXAMPLE 5

4-Cyclohexyloxybenzaldehyde semicarbazone a) 4-Cyclohexyloxybenzaldehyde:

A mixture of 4-hydroxybenzaldehyde (5.2 g), cyclohexyl bromide (25 mL), and potassium carbonate (10 g) in DMF (25 mL) was heated under nitrogen at 90 (C for two days. After cooling, the mixture was diluted with 1:1 hexane/ EtOAc (100 mL), washed with water (2×50 mL), 2 N NaOH (3×15 mL), water (20 mL) and brine (20 mL), dried over $Na_2SO_4$, and concentrated in vacuo to yield the title compound as an oil (2.1 g, 24%). $^1$H NMR (CDCl$_3$): δ 9.86 (s, 1H), 7.82 (d, J=8.5, 2H), 6.98 (d, J=8.5, 2H), 4.38 (m, 1H), 2.01–1.38 (m, 10H).

b) 4-Cyclohexyloxybenzaldehyde semicarbazone:

To a solution of 4-cyclohexyloxybenzaldehyde (2.1 g) in ethanol (50 mL) was added a solution of semicarbazide hydrochloride (1.24 g) and sodium acetate (0.87 g) in water (20 mL) at room temperature. The mixture was stirred for 30 min, and the resulting solid was collected by filtration, washed with water (3×50 mL) and dried in vacuo to yield the title compound as a white solid (2.2 g, 72%), mp: 215 –217° C. $^1$H NMR (DMSO-$d_6$): δ 10.08 (s, 1H), 7.61 (d, J=8.5, 2H), 6.92 (d, J=8.5, 2H), 6.41 (s, 2H), 4.38 (m, 1H), 1.91–1.24 (m, 10H).

EXAMPLE 6

4-Cycloheptyloxybenzaldehyde semicarbazone a) 4-Cycloheptyloxybenzaldehyde:

A mixture of 4-hydroxybenzaldehyde (1.5 g), cycloheptyl bromide (3.5 mL), and potassium carbonate (2.4 g) in N,N-dimethyl acetamide (40 mL) was refluxed under nitrogen for 17 h. After cooling, the mixture was diluted with 1:1 hexane/EtOAc (80 mL), washed with water (2×30 mL), 2 N NaOH (2×20 mL), water (30 mL) and brine (20 mL), dried over $Na_2SO_4$, and concentrated in vacuo to yield the title compound as an oil (1.7 g, 63%). $^1$H NMR (CDCl$_3$): δ 9.86 (s, 1H), 7.80 (m, 2H), 6.91 (m, 2H), 4.38 (m, 1H), 2.04–1.52 (m, 12H).

b) 4—Cycloheptyloxybenzaldehyde semicarbazone:

To a solution of 4-cycloheptyloxybenzaldehyde (1.7 g) in ethanol (20 mL) was added a solution of semicarbazide hydrochloride (0.96 g) and sodium acetate (0.69 g) in water (10 mL) at room temperature. The mixture was stirred for 30 min, and the resulting solid was collected by filtration, washed with water (3×30 mL) and dried in vacuo to yield the title compound as a white solid (1.7 g; 79%), mp: 215–216° C. $^1$H NMR (DMSO-$d_6$): δ 10.07 (s, 1H), 7.76 (s, 1H), 7.61 (d, J=8.4, 2H), 6.89 (d, J=8.4, 2H), 6.40 (s, 2H), 4.54 (m, 1H), 1.98–1.47 (m, 2H).

EXAMPLE 7

4-(5-Indanoxy)benzaldehyde semicarbazone a) 4-(5-indanoxy)benzaldehyde:

A mixture of 4-fluorobenzaldehyde (4.1 mL), 5-indanol (5.2 g), and potassium carbonate (5.5 g) in N,N-dimethylacetamide (30 mL) was refluxed under nitrogen for 17 h. After cooling, the mixture was diluted with 1:1 hexane/EtOAc (100 mL), washed with water (2×30 mL), 2 N NaOH (20 mL), water (30 mL) and brine (20 mL), dried over $Na_2SO_4$, and concentrated in vacuo to yield the title compound as an oil (6.2 g, 68%). $^1$H NMR (CDCl$_3$): δ 9.91 (s, 1H), 7.83 (d, J=8.8, 2H), 7.23 (d, J=7.8, 1H), 7.04 (d, J=8.8, 2H), 6.94 (s, 1H), 6.85 (d, J=7.8, 1H), 2.92 (t, J=7.2, 4H), 2.13 (m, 2H).

b) 4-(5-indanoxy)benzaldehyde semicarbazone:

To a solution of 4-(5-indanoxy)benzaldehyde (6.2 g) in ethanol (100 mL) was added a solution of semicarbazide hydrochloride (3.2 g) and sodium acetate (2.3 g) in water (50 mL) at room temperature. The mixture was stirred for 1 h, and the resulting solid was collected by filtration, washed with water (3×100 mL) and dried in vacuo to yield the title compound as a pale yellow solid (7.5 g, 97%), mp: 218–220° C. $^1$H NMR (DMSO-$d_6$): δ 10.19 (s, 1H), 7.80 (s, 1H), 7.70 (d, J=8.7, 2H), 7.24 (d, J=8.1, 1H), 6.94 (d, J=8.7, 2H), 6.92 (s, 1H), 6.82 (d, J=8.1, 1H), 6.45 (s, 2H), 2.84 (t, J=7.5, 4H), 2.05 (m, 2H).

EXAMPLE 8

4-(4-Fluorophenoxy)benzaldehyde 4'-Metliylsemicarbazone a) 4-Methyl Semicarbazide:

A solution of methyl isocyanate (5.74 mmol, 0.34 mL) in benzene (5 mL) was added dropwise over 10 min to a stirred solution of hydrazine hydrate (0.18 mL, 5.74 mmol) in EtOH (10 mL). Additional benzene (5 mL) was added, and the resulting solution was stirred at rt for 1 h. The precipitate was removed by vacuum filtration and the filtrate was concentrated to give 289 mg (57%) of the title compound as a white solid: $^1$H NMR (DMSO-$d_6$) δ 2.55 (d, 3H), 4.01 (s, 2H), 6.22 (bs, 1H), 6.86 (s, 1H).

b) 4-(4-Fluorophenoxy)benzaldehyde 4'-Methylsemicarbazone:

A solution of 4-methyl semicarbazide (289 mg, 3.28 mmol) and the 4-(4-fluorophenoxy)benzaldehyde (355 mg, 1.64 mmol) in EtOH (20 mL) was stirred at rt overnight. To the solution was added H$_2$O (100 mL), and the mixture was allowed to sit in an ice-bath for 30 min. The precipitate was collected by vacuum filtration to afford 462 mg (98%) of the title compound as a white powder: mp 168–169° C.; $^1$H NMR (DMSO-$d_6$) δ 2.67 (d, 3H), 6.91–6.97 (m, 3H), 7.07–7.11 (m, 2H), 7.21–7.26 (m, 2H), 7.15 (d, 2H), 7.78 (s, 1H 10.26 (s, 1H).

EXAMPLE 9

4-(4-Fluorophenoxy)benzaldeltyde 2'-Methtylsemicarbazone

To a solution of sodium cyanate (1.43 g) in water (15 mL) was added methylhydrazine (1.0 mL). The mixture was stirred at room temperature for 17 h and then acetic acid (2 mL) was added. The mixture was further stirred at room temperature for 3 h and then was added to a solution of 4-(4-fluorophenoxy)benzaldehyde (1.1 g) in ethanol (30 mL) at rt. After 2 h stirring, the resulting solid was collected by filtration, washed with water (3×20 mL) and dried in vacuo to yield the title compound as a white solid (1.4 g, 96%), mp: 153–154° C. $^1$H NMR (DMSO-$d_6$): δ 7.86 (d, J=8.4, 2H), 7.67 (s, 1H), 7.29–7.09 (mn, 4H), 6.99 (d, J=8.4, 2H), 6.65 (br s, 2H), 3.22 (s, 3H)

EXAMPLE 10

4-(Cyclohevxylmetlioxy)benzaldehyde semicarbazone a) 4-(Cyclohexylmethoxy)benzaldehyde.

A mixture of 4-hydroxybenzaldehyde (1.41 g, 11.5 mmol), (bromomethyl)cyclohexane (1.0 mL, 11.5 mmol), and potassium carbonate (3.2 g) in N,N-dimethylacetamide (25 mL) was refluxed for 17 h under nitrogen. After cooling, the mixture was diluted with 1:1 hexane/EtOAc (75 mL), washed with water (2×30 mL), 2 N NaOH (20 mL), water (30 mL) and brine (20 mL), dried over Na$_2$SO$_4$, concentrated in vacuo to yield the title compound as a brown oil (1.6 g, 7.3 mmol, 63%). $^1$H NMR (CDCl$_3$): δ 9.88 (s, 1H), 7.82 (d, J=8.4, 2H), 6.99 (d, J =8.4, 2H), 3.83 (d, J=6.0, 2H), 2.05–1.04 (m, 11H).

b) 4-(Cyclohexylmethoxy)benzaldehyde semicarbazone.

The title compound was prepared in a procedure identical to that given for 4-(5-indanoxy)benzaldehyde semicarbazone in 72% yield, mp: 218–219° C. $^1$H NMR (DMSO-$d_6$): δ 10.07 (s, 1H), 7.77 (s, 1H), 7.62 (d, J=8.5, 2H), 6.92 (d, J=8.5, 2H), 6.40 (s, 2H), 3.80 (d, J=6.3, 2H), 1.82–1.64 (m, 6H), 1.27–1.01 (mn, 5H). Anal. calcd. for C$_{15}$H$_{21}$N$_3$O$_2$: C,65.43: H, 7.69; N, 15.26. Found: C, 65.56; H, 7.59; N, 14.99.

EXAMPLE 11

3-Fluoro-4-(4-fluorophenoxy)benzaldehyde semicarbazone a) 3-Fluoro-4-(4-fluorophenoxy)benzaldehyde.

A mixture of 3,4-difluorobenzaldehyde (4.9 g, 34.5 mmol), 4-fluorophenol (4.0 g, 35.7 mmol), and potassium carbonate (5.0 g, 36.2 mmol) in N,N-dimethylacetamide (30 mL) was refluxed for 5 h under nitrogen. After cooling, the mixture was diluted with 1:1 hexane/EtOAc (75 mL), washed with water (2×30 mL), 2 N NaOH (20 mL), water (30 mL) and brine (20 mL), dried over Na$_2$SO$_4$, decolorized with activated charcoal, and concentrated in vacuo to yield the title compound as an oil (6.1 g, 26.0 mmol, 75%). $^1$H NMR (CDCl$_3$): δ 9.89 (d, J=2.1, 1H), 7.72–7.57 (mn, 2H), 7.13–6.93 (m, 4H).

b) 3-Fluoro-4-(4-fluorophenoxy)benzaldehyde semicarbazone.

The title compound was prepared using the procedure described for 4-(5-indanoxy)benzaldehyde semicarbazone in 80% yield, mp: 233–234° C. $^1$H NMR (DMSO-$d_6$): δ 10.32 (s, 1H), 7.95 (d, J=12.6, 1H), 7.80 (s, 1H), 7.43 (d, J=9.0, 1H), 7.27–7.21 (m, 2H), 7.11–7.05 (m, 3H), 6.54 (s, 2H). Anal Calcd. for C$_{14}$H$_{11}$N$_3$O$_2$: C, 57.73; H, 3.81; N, 14.43. Found: C, 57.84; H, 3.62; N, 13.81.

EXAMPLE 12

4-(4-Tetrahydropyranoxy)benzaldehyde semicarbazone a) 4-(4-Tetrahydropyranoxy)benzaldehyde.

A mixture of 4-hydroxybenzaldehyde (2.0 g, 16.4 mmol), 4-chlorotetrahydropyran (3.6 mL, 32.8 mmol), and potassium carbonate (4.5 g, 32.6 mmol) in N,N-dimethylacetamide (30 mL) was refluxed for 20 h under nitrogen. After cooling, the mixture was diluted with 1:1 hexane/EtOAc (120 mL), washed with water (2×30 mL), 2 N NaOH (2×20 mL), water (30 mL) and brine (20 mL), dried over Na$_2$SO$_4$, concentrated in vacuo to yield the title compound as a yellow oil (1.0 g, 4.8 mmol, 29%). $^1$H NMR (CDCl$_3$): δ 9.87 (s, 1H), 7.83 (d, J=8.5, 2H), 7.00 (d, J=8.5, 2H), 4.62 (m, 1H), 4.02–3.57 (m, 4H), 2.08–1.77 (m, 4H).

b) 4-(4-Tetrahydropyranoxy)benzaldehyde semicarbazone.

The title compound was prepared in a procedure identical to that given for 4-(5-indanoxy)benzaldehyde semicarbazone in 71% yield, mp: 208–209° C. $^1$H NMR (DMSO-$d_6$): δ 10.08 (s, 1H), 7.77 (s, 1H), 7.80 (s, 1H), 7.63 (d, J=8.6, 2H), 6.98 (d, J=8.6, 2H), 6.40 (s, 2H), 4.62 (p, 1H), 3.88–3.81 (m, 2H) 3.53–3.45 (m, 2H), 1.99–1.94 (m, 2H), 1.63–1.52 (m, 2H).

EXAMPLE 13

4-(1-Methyl-4-piperidinoxy)benzaldehyde semicarbazone a) 4-(1-Methyl-4-piperidinoxy)benzaldehyde.

A mixture of 4-hydroxybenzaldehyde (2.0 g, 16.4 mmol), 1-methyl-4-chloropiperidine hydrochloride (3.3 g, 19.4 mmol), and potassium carbonate (8.1 g, 58.6 mmol) in N,N-dimethylacetamide (30 mL) was refluxed for 20 h under nitrogen. After cooling, the mixture was diluted with EtOAc (120 mL), washed with water (2×30 mL), 2 N NaOH (2×20 mL), water (30 mL) and brine (20 mL), dried over $Na_2SO_4$, concentrated in vacuo to yield the title compound as a yellow oil (0.52 g, 2.4 mmol, 14%). $^1$H NMR ($CDCl_3$): 9.87 (s, 1H), 7.82 (d, J=9.0, 2H), 6.99 (d, J=9.0, 2H), 4.44 (m, 1H), 2.99 (m, 2H), 2.33–2.06 (m, 2H), 2.31 (s, 3H), 2.06–1.92 (m, 2H).

b) 4-(1-Methyl-4-piperidinoxy)benzaldehyde semicarbazone.

To a solution of 4-(4-tetrahydropyranoxy)benzaldehyde (120 mg, 0.55 mmol) in ethanol (4 mL) was added a solution of semicarbazide hydrochloride (118 mg, 1.06 mmol) and sodium acetate (90 mg, 1.1 mmol) in water (2 mL) at room temperature. After 2 h stirring, the solvent was removed in vacuo. To the residue was added EtOH (20 mL). The resulting solid was isolated by filtration. The filtrate was concentrated in vacuo to yield the product as a white solid (110 mg) which is moisture sensitive. $^1$H NMR (DMSO-$d_6$): δ 10.05 (s, 1H), 7.75 (s, 1H), 7.59 (d, J=8.7, 2H), 6.92 (d, J=8.7, 2H), 6.37 (s, 2H), 4.83 (m, 1H), 2.61–2.54 (m, 2H), 2.18–2.12 (m, 2H), 2.15 (s, 3H 1.92–1.85 (m, 2H), 1.64–1.58 (m, 2H).

EXAMPLE 14

4-(exo-2-Norbornoxy)benzaldelhyde semicarbazone a) 4-(exo-2-Norbornoxy)benzaldehyde.

A mixture of 4-hydroxybenzaldehyde (2.1 g, 17.2 mmol), exo-2-bromonorbonane (4.4 mL, 34.2 mmol), and potassium carbonate (5.2 g, 37.6 mmol) in N,N-dimethylacetamide (30 mL) was refluxed for 5 h under nitrogen. After cooling, the mixture was diluted with 1:1 hexane/EtOAc (80 mL), washed with water (2×30 mL), 2 N NaOH (2×20 mL), water (30 mL) and brine (20 mL), dried over $Na_2SO_4$, concentrated in vacuo to yield the title compound as an oil (3.3 g, 15.3 mmol, 89%). $^1$H NMR ($CDCl_3$): δ 9.86 (s, 1H), 7.80 (d, J=9.0, 2H), 6.96 (d, J=9.0, 2H), 4.67 (m, 1H), 2.62–1.11 (m, 10H).

b) 4-(exo-2-Norbornoxy)benzaldehyde semicarbazone.

The title compound was prepared in a procedure identical to that given for 4-(5-indanoxy)benzaldehyde semicarbazone in 78% yield. mp: 211–212° C. $^1$HNMR (DMSO-$d_6$): δ 10.07 (s, 1H), 7.76 (s, 1H), 7.61 (d, J=8.8, 2H), 6.89 (d, J=8.8, 2H), 6.40 (s, 2H), 4.69–4.66 (m, 1H), 2.54–0.95 (m, 10H).

EXAMPLE 15

4-(4-Nitrophenoxy)benzaldehiyde semicarbazone a) 4-(4-Nitrophenoxy)benzaldehyde.

A mixture of 4-fluorobenzaldehyde (4 mL, 37.4 mmol), 4-nitrophenol (5.2 g, 37.4 mmol), and potassium carbonate (5.3 g, 38.8 mmol) in N,N-dimethylacetamide (30 mL) wvas refluxed for 24 h under nitrogen. After cooling, the mixture was diluted with 1:1 hexane/EtOAc (80 mL), washed with water (2×30 mL), 2N NaOH (2×20 mL), water (30 mL) and brine (20 mL), dried over $Na_2SO_4$, concentrated in vacuo. The residue was purified by chromatography to yield the title compound as light yellow solid (2.1 g, 8.6 mmol, 23%). $^1$H NMR ($CDCl_3$): δ 10.00 (s, 1H), 8.28 (d, J=9.0, 2H), 7.96 (d, J=8.7, 2H), 7.20 (d, J=8.7, 2H), 7.15 (d, J=9.0, 2H).

b) 4-(4-Nitrophenoxy)benzaldehyde semicarbazone.

The title compound was prepared in a procedure identical to that given for 4-(5-indanoxy)benzaldehyde semicarbazone in 93% yield, mp: 221–222° C. $^1$H NMR (DMSO-$d_6$): δ 10.28 (s, 1H), 8.27 (d, J=9.0, 2H), 7.87 (s, 1H), 7.85 (d, J=9.0, 2H), 7.21–7.16 (m, 4H), 6.51 (s, 2H). Anal Calcd. for $C_{14}H_{12}N_4O$: C, 56.00; H, 4.03; N, 18.66. Found: C, 55.96; H, 4.05; N, 18.36.

EXAMPLE 16

4-(2-Fluorobenzyloxy)benzaldehyde semicarbazone a) 4-(2-Fluorobenzyloxy)benzaldehyde.

A mixture of 4-hydroxybenzaldehyde (2.0 g, 16.4 mmol), 2-fluorobenzylchloride (1.9 mL, 16.0 mmol), and potassium carbonate (3.6 g, 26.0 mmol) in N,N-dimethylacetamide (30 mL) was refluxed for 5 h under nitrogen. After cooling, the mixture was diluted with 1:1 hexane/EtOAc (80 mL), washed with water (2×30 mL), 2N NaOH (2×20 mL), water (30 mL) and brine (20 mL), dried over $Na_2SO_4$, concentrated in vacuo to yield the title compound as a yellow solid (3.5 g, 15.2 mmol, 93%). $^1$H NMR ($CDCl_3$): δ 9.90 (s, 1H), 7.86(d, J=8.7, 2H), 7.52–7.15 (m, 4H), 7.10 (d, J=8.7, 2H), 5.22 (s, 2H)

b) 4-(2-Fluorobenzyloxy)benzaldehyde semicarbazone.

The title compound was prepared in a procedure identical to that given for 4-(5-indanoxy)benzaldehyde semicarbazone in 86% yield, mp: 211–212° C. $^1$H NMR (DMSO-$d_6$): δ 10.11 (s, 1H), 7.79 (s, 1H), 7.67 (d, J=8.8, 2H), 7.59–7.54 (m, 1H), 7.48–7.40 (m, 1H), 7.29–7.22 (m, 2H), 7.05 (d, J=8.8, 2H), 6.43 (s, 2H), 5.17 (s,2H). Anal. Calcd. for $C_{15}H_{14}N_3O_2$: C, 62.71; H, 4.91; N, 14.63. Found: C, 62.61; H, 4.93; N, 14.51.

EXAMPLE 17

4-(5,6,7,8-Tetrahydro-2-naphthoxy)benzaldehyde semicarbazone

The title compound was prepared in a procedure identical to that given for 4-(5-indanoxy)benzaldehyde semicarbazone in 68% yield, mp: 202–204° C. $^1$H NMR (DMSO-$d_6$): δ 10.18 (s, 1H), 7.80 (s, 1H), 7.70 (d, J=8.8, 2H), 7.09 (d, J=8.1, 1H), 6.94 (d, J=8.8, 2H), 6.80–6.75 (m, 2H), 6.45 (s,2H), 2.69 (s, 4H), 1.72 (s, 4H).

EXAMPLE 18

4-(2-Adamantanoxy)benzaldehyde semicarbazone

The title compound was prepared in a procedure identical to that given for 4-(5-indanoxy)benzaldehyde semicarbazone in 58% yield, mp: 226–228° C. $^1$H NMR (DMSO-$d_6$): δ 10.08 (s, 1H), 7.77 (s, 1H), 7.62 (d, J=8.5, 2H), 6.96 (d, J=8.5, 2H), 6.41 (s, 2H), 4.85 (s, 1H), 4.55 (s,1H), 2.22–1.48 (m, 13H

EXAMPLE 19

4-(2,4,6-Trimethylphenoxy)benzaldehyde semicarbazone

The title compound was prepared in a procedure identical to that given for 4-(5-indanoxy)benzaldehyde semicarbazone in 66% yield, mp: 189–190° C. $^1$H NMR (DMSO-$_6$): δ 10.13 (s, 1H), 7.78 (s, 1H), 7.64 (d, J=8.7, 2H), 6.98 (s, 2H), 2.27 (s, 3H), 2.01 (s, 6H).

EXAMPLE 20

2-Fluoro4-(4-fluorophenoxy)acetophenone semicarbazone

The title compound was prepared in a procedure identical to that given for 4-(5-indanoxy)benzaldehyde semicarbazone in 75% yield, mp: 218–220° C.

$^1$H NMR (DMSO-$d_6$): δ 9.36 (s, 1H), 8.01 (d, J=12.9, 1H), 7.62 (d, J=9.0, 1H), 7.26–7.04 (m, 5H), 6.57 (s, 2H), 2.17 (s, 3H).

EXAMPLE 21

4-(4-Fluorophenoxy)benzaldehyde [1-(carboxymethyl)trimethylammonium chloride] hydrazone To a solution of 4-(4-fluorophenoxy)benzaldehyde (337 mg, 1.56 mmol) in ethanol (10 mL) was added a solution of [1-(carboxymethyl)trimethylammonium chloride]hydrazine (263 mg, 1.57 mmol) in water (5 mL) at room temperature. The mixture wNas stirred at room temperature for 3 days, concentrated in in vacuo to about 2 mL and washed with EtOAc (2×10 mL). The aqueous solution was concentrated to yield a white solid (228 mg, 0.59 nmmol, 38%), mp: 207–209 ° C. NMR indicated that product consisted of two isomers. $^1$H NMR (major isomer, DMSO-$d_6$): δ 12.05 (s, 1H), 8.09 (s, 1H), 7.74 (d, J=7.2, 2H), 7.31–7.12 (m, 4H), 7.05 (d, J=7.2, 2H), 4.79 (s, 2H), 3.32 (s, 9H).

EXAMPLE 22

4-(4-Fluorophenoxy)benzaldehyde carbomethoxyhydrazone

To a solution of 4-(4-fluorophenoxy)benzaldehyde (277 mg, 1.28 mmol) in ethanol (10 mL) was added a solution of carbomethoxyhydrazine (180 mg, 2.0 mmol) in water (5 mL), followed by AcOH (0.1 mL) at room temperature. The mixture was stirred at room temperature for 17 h and water (20 mL) was added. The resulting solid was collected by filtration, washed with water and dried in vacuo to yield the title compound as a white solid (228 mg, 0.74 mmol, 58%), mp: 109–111° C. $^1$H NMR (DMSO-$d_6$): δ 11.05 (s, 1H), 8.00 (s, 1H), 7.64 (d, J=8.7, 2H), 7.30–6.99 (m, 6H), 3.69 (s, 3H).

EXAMPLE 23

The following semicarbazones were prepared according to the procedure described for 4-(5-indanoxy)benzaldehyde semicarbazone, starting with the necessary commerically available aldehydes:

Piperonal semicarbazone: mp 227–229C; $^1$H NMR (DMSO-$d_6$) δ 6.02 (s, 2H), 6.46 (bs, 2H), 6.88 (d, J=7.8, 1H), 7:71 6.98–7.01 (m, 1H), 7.50 (s, 1H) (s, 1H), 10.1 (s, 1H).

6-Chloropiperonal semicarbazone: $^1$H NMR (DMSO-$d_6$) δ 6.08 (s, 2H), 6.58 (bs, 2H), 7.06 (s, 1H), 7.78 (s, 1H), 8.10 (s, 1H), 10.3 (s, 1H).

1,4-Benzodioxane-6-carboxaldehyde semicarbazone: mp 217–220° C.; $^1$H NMR (DMSO-$d_6$) δ 4.23 (s, 4H), 6.41 (bs, 2H), 6.81–6.83 (m, 1H), 7.12 (d, J=8.4, 1H), 7.26 (s, 1H), 7.68 (s, 1H), 10.1 (s, 1H).

5-Bromo-2-hydroxy-3-methoxybenzaldehyde semicarbazone: $^1$H NMR (DMSO-$d_6$) δ 3.80 (s, 3H), 6.51 (bs, 2H), 7.03 (d, J=2.7, 1H), 7.67 (d, J=2.4, 1H), 8.08 (s, 1H), 9.44 (bs, 1H), 10.3 (s, 1H).

6-Methoxy-2-naphthaldehyde semicarbazone: mp 268–289° C.; $^1$H NMR (DMSO-$d_6$) δ 3.86 (s, 3H), 6.50 (bs, 2H), 7.14–7.17 (m, 1H), 7.32 (d, J=2.4, 1H), 7.76–7.83 (m, 2H), 7.93 (s, 2H), 8.00–8.02 (s, J=8.4, 1H), 10.3 (s, 1H).

4-Dimethylamino-1-naphthaldehyde semicarbazone: mp 218–219° C.; $^1$H NMR (DMSO-$d_6$) δ 2.84 (s, 6H), 6.42 (s, 2H), 7.10 (d, J=8.1, 1H), 7.50–7.61 (m, 2H), 7.89 (d, J=7.8, 1H), 8.16–8.19 (m, 1H), 8.45 (d, J=8.1, 1H), 8.50 (s, 1H), 10.2 (s, 1H).

2-Naphthaldehyde semicarbazone: mp 241–245° C.; $^1$H NMR (DMSO-$d_6$) 866.55 (bs, 2H), 7.47–7.53 (m, 2H), 7.86–7.92 (m, 3H), 7.99 (d, J=8.4, 2H), 8.06–8.09 (m, 1H), 10.3 (s, 1H).

3-Quinolinecarboxaldehyde semicarbazone: mp 250–253° C.; $^1$H NMR (DMSO-$d_6$) δ 6.65 (bs, 2H), 7.58–7.63 (m, 1H), 7.70–7.76 (m, 1H), 7.93–8.01 (m, 3H), 8.49 (d, J=1.5, 1H), 9.41 (d, J=2.1, 1H), 10.5 (s, 1H).

1-Methylindole-3-carboxaldehyde semicarbazone: mp 196–199° C.

2,4,6-Trimethoxybenzaldehyde semicarbazone: mp 205–209° C.

3,4,5-Trimethoxybenzaldehyde semicarbazone: mp 210–214° C.

Mesitaldehyde semicarbazone: mp 192–195° C.

2,2-Difluoro-5-formylbenzodioxole semicarbazone: mp 219–223° C.

5-Indancarboxaldehyde semicarbazone: mp 217–220° C.

Pentafluorobenzaldehyde semicarbazone: mp 164–166° C.

6-Nitropiperonal semicarbazone: $^1$H NMR (DMSO-$d_6$) δ 6.23 (s, 2H), 6.66 (bs, 2H), 7.57 (s, 1H), 7.93 (s, 1H), 8.24 (s, 1H), 10.5 (s, 1H).

4-Biphenylcarboxaldehyde semicarbazone: $^1$H NMR (DMSO-$d_6$) δ 6.50 (bs, 2H), 7.33–7.38 (m, 1H), 7.43–7.48 (m, 2H), 7.65–7.70 (m, 4H), 7.79 (d, J=8.4, 2H), 7.86 (s, 1H), 10.3 (s, 1H).

3,5-Dimethyl-4-hydroxybenzaldehyde semicarbazone: mp 200–205° C.

Indole-3-carboxaldehyde semicarbazone: mp 207–209° C.

Cyclohexanecarboxaldehyde semicarbazone: mp 163–168° C.

Isobutyaldehyde semicarbazone: mp 123–124° C.

4-(6-Bromo-4-fluorophenoxy)benzaldehyde semicarbazone: mp 202–205° C.

4-(N,N-Diphenylamino)benzaldehyde semicarbazone: mp 106–114° C.

2-(4—Chlorophenylthio)benzaldehyde semicarbazone: mp 206–209° C.

4-Trifluoromethylbenzaldehyde semicarbazone: $^1$H NMR (DMSO-$d_6$) δ 6.60 (bs, 2H), 7.70 (d, J=8.1, 2H), 7.87 (s, 1H), 7.93 (d, J 8.1, 2H), 10.5 (s. 1H).

Dibenzofuran-x-carboxaldehyde semicarbazone: $^1$H NMR (DMSO-$d_6$) δ 6.56 (bs, 2H), 7.42 (t, J=7.4, 1H), 7.53 (t, J=7.5, 1H), 7.67–7.74 (m, 2H), 7.90 (d, J=8.4, 1H), 7.98 (s, 1H), 8.15 (d, J=7.8, 1H), 8.52 (s, 1H), 10.3 (s, 1H).

2-Fluorenecarboxaldehyde semicarbazone: $^1$H NMR (DMSO-$d_6$) δ 3.92 (s, 2H), 6.50 (bs, 2H), 7.29–7.40 (m, 2H), 7.58 (d, J=6.9, 1H), 7.68 (d, J=7.8, 1H), 7.89 (t, J=6.6, 3H), 7.96 (s, 1H), 10.2 (s, 1H).

2-Trifluoromethylbenzaldehyde semicarbazone: mp 226–230° C.

3-Trifluoromethylbenzaldehyde semicarbazone: mp 206–209° C.

Diphenylacetaldehyde semicarbazone: mp 146–150° C.

Piperonal 2'-methylsemicarbazone: mp 224–228° C.

2,2-Difluoro-5-formylbenzodioxole 2'-methylsemicarbazone: mp 141–143° C.

1,4-Benzodioxane-6-carboxaldehyde 2'-methylsemicarbazone: mp 213–220° C.

6-Chloropiperonal 2'-methylsemicarbazone: mp 235–237° C.

6-Nitropiperonal 2'-methylsemicarbazone: mp 265–266° C.

4-Biphenylcarboxaldehyde 2'-methylsemicarbazone: mp 239–242° C.

3-Quinolinecarboxaldehyde 2'-methylsemicarbazone: mp 174–176° C.

2-Naphthaldehyde 2'-methylsemicarbazone: mp 204–208° C.

4-Dimethylamino-1-naphthaldehyde 2'-methylsemicarbazone: mp 163–165° C.

6-Methoxy-2-naphthaldehyde 2'-methylsemicarbazone: mp 212–213° C.

5-Indancarboxaldehyde 2'-methylsemicarbazone: mp 143–150° C.

Indole-3-carboxaldehyde 2'-methylsemicarbazone: mp 230–234° C.

1-Methylindole-3-carboxaldehyde 2'-methylsemicarbazone: mp 200–201° C.

4-Phenoxybenzaldehyde 2'-methylsemicarbazone: mp 162–167° C.

3-Phenoxybenzaldehyde 2'-methylsemicarbazone: mp 126–128° C.

Pentafluorobenzaldehyde 2'-methylsemicarbazone: mp 169–190° C.

5-Bromo-2-hydroxy-3-methoxybenzaldehyde 2'-methylsemicarbazone: mp 177–182° C.

Mesitaldehyde 2'-methylsemicarbazone: mp 175–179° C.

2,4,6-Trimethoxybenzaldehyde 2'-methylsemicarbazone: mp 160–162° C.

3-Hydroxy-4-methoxybenzaldehyde 2'-methylsemicarbazone: mp 197–199° C.

3,4-Dimethoxybenzaldehyde 2'-methylsemicarbazone: mp 122–130° C.

3,4-Difluorobenzaldehyde 2'-methylsemicarbazone: mp 158–160° C.

4-Trifluoromethylbenzaldehyde 2'-methylsemicarbazone: mp 162–164° C.

4-Trifluoromethoxybenzaldehyde 2'-methylsemicarbazone: mp 161–163° C.

EXAMPLE 24

4-(4-Fluorophenoxy)benzaldehyde 2'-butylsemicarbazone

To a solution of sodium cyanate (374 mg, 5.75 mmol) in $H_2O$ (5 mL) was added butylhydrazine oxalate (891 mg, 5.0 mmol) and $H_2O$ (7 mL). The resulting mixture was stirred at rt overnight, then concentrated to near dryness. To this residue was added 4-(4-fluorophenoxy)benzaldehyde (216 mg, 1.0 mmol), EtOH (20 mL), and $H_2O$ (10 mL), and the mixture was fuirther stirred at rt overnight. The precipitate was collected by vacuum filtration. Hot filtration of the precipitate in MeOH, followed by flash chromatography using 7:3 $CHCl_3$/EtOAc with few drops of TEA per 100 mL of the solvent mixture gave 74 mg (22%) of the title compound as a white powder: $^1$H NMR (DMSO-$d_6$) δ 0.88 (t, J=7.2, 3H), 1.24–1.44 (m, 4H), 3.85 (t, J=7.2, 2H), 6.68 (bs, 2H), 6.96 (d, J=8.7, 2H), 7.07–7.11 (m, 2H), 7.21–7.27 (m, 2H) 7.70 (s, 1H), 7.85 (d, J=8.4, 2H).

EXAMPLE 25

4-(4-Fluorophenoxy)benzaldehyde 4'-ethylsemicarbazone a) 4-Ethyl Semicarbazide:

A solution of ethyl isocyanate (0.45 mL, 5.74 mmol) in benzene (5 mL) was added dropwise to a stirred solution of hydrazine hydrate (0.18 mL, 5.74 mmol) in EtOH (10 mL). The resulting solution was stirred at rt for lh. The precipitate was removed by vacuum filtration and the filtrate was concentrated to give 461 mg (78%) of the title compound as a clear liquid: $^1$H NMR ($CDCl_3$) δ 1.10 (t, J=7.2, 3H), 3.16–3.25 (m, 2H), 3.65 (bs, 2H), 6.04 (bs, 1H), 6.87 (s, 1H).

b) 4-(4-Fluorophenoxy)benzaldehyde 4'-ethylsemicarbazone:

A solution of 4-ethyl semicarbazide (210 mg, 2.04 mmol) and 4-(4-fluorophenoxy)benzaldehyde (435 mg, 2.01 mmol) in EtOH (20 mL) with few drops of acetic acid was stirred at rt for 1 h. To the solution was added $H_2O$ (100 mL), and the mixture was allowed to sit in an ice-bath for 30 min. The precipitate was collected by vacuum filtration, then recrys- tallized from EtOAC/$H_2O$ to afford 372 mg (61%) of the title compound as a white powder: mp 148–149° C.; $^1$H NMR (DMSO-$d_6$) δ 1.05 (t, J=7.2, 3H), 3.10–3.19 (m, 2H), 6.94–6.99 (m, 3H), 7.07–7.11 (m, 2H), 7.21–7.26 (m, 2H), 7.72 (d, J=8.4, 2H), 7.78 (s, 1H), 10.22 (s, 1H).

EXAMPLE 26

4-(4-Fluorophenoxy)benzaldehyde 4',4'-dimethylsemicarbazone a) 4,4-Dimethyl Semicarbazide:

To a stirred solution of hydrazine hydrate (441 mg, 13.8 mmol) in EtOH (20 mL) was added a solution of dimethylcarbamyl chloride (1.27 mL, 13.8 mmol) in $Et_2O$ (10 mL) dropwise over 18 min in an ice-bath. The resulting solution was stirred in the ice-bath for 1h. The precipitate was removed by vacuum filtration and the filtrated was concentrated to give a white solid which was recrystallized from EtOAC/$CH_2Cl_2$ to yield 534 mg (38%) of the title compound: $^1$H NMR (DMSO-$d_6$) δ 2.81 (d, J=18.0, 6H), 7.90 (s, 1H), 9.30 (s, 1H), 9.91 (bs, 1H).

b) 4-(4-Fluorophenoxy)benzaldehyde 4',4'-dimethylsemicarbazone:

A solution of 4-dimethyl semicarbazide (150 mg, 1.46 mmol) and 4-(4-fluorophenoxy)benzaldehyde (300 mg, 1.39 mmol) in EtOH (20 mL) with few drops of acetic acid was stirred at rt for 2 h. To the solution was added $H_2O$ (80 mL), and the mixture was allowed to sit in an ice-bath for 30 min. The precipitate was collected by vacuum filtration, then recrystallized from EtOAC/$CHCl_3$ to afford 19 mg (4.5 %) of the title compound as a white powder: mp 70–71° C.; $^1$H NMR (DMSO-$d_6$) δ 2.87 (s, 6H), 6.98 (d, J=9.0, 2H), 7.08–7.12 (m, 2H), 7.21–7.27 (m, 2H), 7.59 (d, J=8.4, 2H), 8.12 (s, 1H), 10.1 (s, 1H).

EXAMPLE 27

4-(4-Fluorophenoxy)benzaldehyde 4',4'-diethylsemicarbazone a) 4,4-Diethyl Semicarbazide:

To a stirred solution of hydrazine hydrate (432 mg, 13.5 mmol) in EtOH (20 m/L) was added a solution of diethylcarbamyl chloride (1.7 mL, 13.5 mmol) in $Et_2O$ (10 mL) dropwise over 6 min in an ice-bath. The resulting solution was stirred in the ice-bath for 1h. The precipitate was removed by vacuum filtration and the filtrated was concentrated, then triturated in $Et_2O$ to give 592 mg (33%) of the title compound as an off white solid: $^1$H NMR (DMSO-$d_6$) δ 0.98–1.06 (m, 6H), 3.15–3.27 (m, 4H), 7.81 (s, 1H), 9.30 (s, 1H), 9.91 (bs, 1H).

b) 4-(4-Fluorophenoxy)benzaldehyde 4',4'-diethylsemicarbazone:

A solution of 4-diethyl semicarbazide (191 mg, 1.46 mmol) and 4-(4-fluorophenoxy)benzaldehyde (300 mg, 1.39 mmol) in EtOH (20 mL) with few drops of acetic acid was stirred at rt for 2 h. Excess 4-diethyl semicarbazide (173 mg, 1.32 mmol) was added and the resulting solution was further stirred at rt overnight. To the solution was added ice $H_2O$ (80 mL), and the mixture was allowed to sit in an ice-bath for 30 min. The precipitate was collected by vacuum filtration, then recrystallized from EtOAc/hexane to afford 268 mg (59%) of the title compound as a pale yellow powder: mp 69–73° C.; $^1$H NMR (DMSO-$d_6$) δ 1.05 (t, J=7.1 Hz, 6H), 3.24–3.31 (m, 4H), 6.98 (d, J=8.7 Hz, 2H), 7.08–7.13 (m, 2H), 7.21–7.27 (m, 2H), 7.58 (d, J=8.7, 2H), 8.14 (s, 1H), 10.0 (s, 1H)

EXAMPLE 28

4-(4-Fluorophenoxy)benzaldeltyde 2'-(etitoxycarbonylmethyl)semicarbazone 4-(4-fluorophenoxy)benzaldehyde semicarbazone (0.330 g, 2.12 mmol) was dissolved in DMF (20 mL). Sodium hydride (60% in dispersion oil, 57.5 mg, 1.44 imnol) was added to the solution. The solution was stirred at room temperature for 10 minutes, then ethyl bromoacetate (0.3 mL, 2.7 mmol) was injected. The solution was stirred for 5.5 hours, then water was added to quench the reaction. The solution was diluted with ethyl acetate, then washed with water several times to remove DMF. After evaporating off the solvent, the crude product was purified by column chromatography. The more polar product (87 mg) was identified as the title compound, mp 147–149° C. $^1$H NMR (CDCl$_3$): δ 7.82 (d, J=8.4 Hz, 2H), 7.55 (s, 1H), 7.24 (t, J=8.7 Hz, 2H), 7.12–7.07 (m, 2H), 6.96 (d, J=8.4 Hz, 2H), 6.80 (bs, 2H), 4.72 (s, 2H) 4.15–4.08 (m, 2H), 1.19 (t, J=6.9, 3H).

EXAMPLE 29

4-(4-Fluorophenoxy)benzaldehtyde 2',4'-propylenesemicarbazone a) 4-(4-fluorophenoxy)benzaldehyde 2'-(3-bromopropyl)semicarbazone.

4-(4-fluorophenoxy)benzaldehyde semicarbazone (0.35 g, 1.38 mmol) and sodium hydride (60% in dispersion oil, 57 mg, 1.42 mmol) were dissolved in DMF. After stirring for 10 minutes, 1,3-dibromopropane (2.0 mL, 19.7 mmol) was added. The solution was stirred until the yellow solution turned white or colorless. The reaction was diluted with ethylacetate/hexane (150 mL), and washed several times with water, then evaporated to dryness. The crude product was purified by column chromatography. The title product was identified by $^1$H NMR (242 mg). $^1$H NMR (CDCl$_3$): δ 7.70 (s, 1H), 7.59 (d, J=9 Hz, 2H), 7.09–7.00 (m, 6H), 4.12 (t, J=6.6 Hz, 2H), 3.49 (t, J=6.0 HZ, 2H), 2.22–2.13 (m, 2H).

b) 4-(4-Fluorophenoxy)benzaldehyde 2',4'-propylenesemicarbazone.

The product from a) (242 mg, 0.614 mmol), and sodium hydride (60% in dispersion oil; 26 mg, 0.65 mmol) were dissolved in 25 mL of DMF at room temperature. The solution was stirred for 2 hours. The reaction was then diluted with ethyl acetate (150 mL), washed three times with water, dried over sodium sulfate, and evaporated under reduce pressure to give crude product.

Purification by column chromatography gave the title compound (72 mg) mp 201–203° C. $^1$H NMR (CDCl$_3$): δ 7.84 (s, 1H), 7.69 (d, J=8.7 Hz, 2H), 7.06–6.91 (m, 6H), 6.22 (bs, 1H), 3.68 (t, J=6 Hz, 2H), 3.35 (bs, 2H), 2.17 (t, J=5.1 Hz, 2H).

EXAMPLE 30

4-(4-Methylphenoxy)benzaldehyde 2'-methylsemicarbazone a) 4-(4-methylphenoxy)benzaldehyde.

Paracresol (5 mL, 47.8 mmol), potassium carbonate (7.95 g, 0.58 mol), and 4-fluorobenzaldehyde (4.3 mL, 40 mmol) in N,N-dimethylactearnide were refluxed under nitrogen for 15 hours. The solution was cooled to room temperature, then diluted with hexane/ethyl acetate (1:1 ratio, 100 mL), washed with water (250 mL), aqueous sodium hydroxide (2 N, 50 mL), brine (50 mL), dried over sodium sulfate, and finally evaporated under reduce pressure to give oil product (9.72 g). $^1$H NMR (CDCl$_3$): δ 9.91 (s, 1H), 7.83 (d, J=8.7, 2H), 7.21 (d, J=8.1, 2H), 7.03 (d, J=8.7, 2H), 6.98 (d, j=8.4, 2H), 2.38 (s, 3H).

b) 4-(4-methylphenoxy)benzaldehyde 2'-methylsemicarbazone.

A solution of 4-(4-methylphenoxy)benzaldehyde (0.2 g) in EtOH (5 mL) was mixed with 2'-methylsemicarbazone solution (0.156 g) in 2 ml of water containing a few drops of acetic acid. After stirring for two hours, the precipitate was isolated by vacuum filtration, washed with water, and dried in vacuo to give 152 mg (57%) of the title compound, mp: 174–176° C. $^1$H NMR (CDCl$_3$): δ 7.58 (d, J=8.7, 2H), 7.52 (s, 1H), 7.17 (d, J=8.1, 2H), 6.98 (d, J=8.7, 2H), 6.95 (d, J=8.7, 2H), 3.36 (s, 3H), 2.35 (s, 3H).

EXAMPLE 31

4-(4-Fluoro-2-chlorophenoxy)benzaldehyde semicarbazone 4-(4-Fluoro-2-chlorophenoxy)benzaldehyde (204 mg, 0.814 mmol), prepared as described for 4-(4-methylphenoxy)benzaldehyde, was dissolved in ethanol (5 mL). An aqueous solution of semicarbazide hydrochloride (2 mL, 1.40 mmol), and sodium acetate (1.30 mmol) were added to the solution. After stirring at rt for several hours, a precipiate formed. The mixture was filtered to isolate the solid, which after drying weighed 206 mg (82%), mp 196–199° C. $^1$H NMR (DMSO-d$_6$): δ 10.17 (s, 1H), 7.78 (s, 2H), 7.70 (d, J=8.4 Hz, 2H), 7.66–7.62 (m, 1H), 7.28–7.25 (m, 2H), 6.89 (d, J=8.4 Hz, 2H), 6.44 (bs, 2H).

The following molecules were prepared in a similar ways as described for 4-(4-methylphenoxy)benzaldehyde 2'-methylsemicarbazone or 4-(4-fluoro-2-chlorophenoxy) benzaldehyde semicarbazone.

4-(3,4-Methylenedioxyphenoxy)benzaldehyde 2'-methylsemicarbazone, mp 197–199° C., $^1$H NMR (CDCl$_3$): δ 7.58 (d, J=8.4, 2H), 7.52 (s, 1H), 6.97 (d, J=8.7, 2H), 6.79 (d, J=8.1, 1H), 6.60 (d, J=2.4, 1H), 6.54–6.51 (m, 1H), 6.00 (s, 2H), 3.36 (s, 3H).

4-(5-Indanoxy)benzaldehyde 2'-methylsemicarbazone, mp 163–165° C., $^1$H NMR (CDCl$_3$): δ 7.58 (d, J=8.4, 2H), 7.52 (s, 1H), 7.19 (d, J=7.2, 1H), 6.99 (d, J=8.7, 2H), 6.91 (s, 1H), 6.84–6.81 (m, 1H), 3.36 (s, 3H), 2.90 (t, J=7.5, 4H), 2.16–2.08 (m, 2H).

4-(2-Chloro-4-fluorophenoxy)benzaldehyde 2'-methylsemicarbazone, mp 185–186° C., $^1$H NMR (DMSO-d$_6$): δ 7.85 (d, J=9.0, 2H), 7.67 (s, 1H), 7.64 (s, 1H), 7.28 (m, 2H), 6.93 (d, J=8.4, 2H), 6.60 (bs, 2H), 3.22 (s, 3H).

4-(4-Chlorophenoxy)benzaldehyde 2'-methylsemicarbazone, mp 160–162° C., $^1$H NMR (CDCl$_3$): δ 7.61 (d, J=9.0, 2H), 7.53 (s, 1H), 7.32 (d, J=8.7, 2H) 6.99 (t, J=8.4, 4H), 3.36 (s, 3H).

4-(3,5-Difluorophenoxy)benzaldehyde 2'-methylsemicarbazone, mp 185–187° C., $^1$H NMR (CDCl$_3$): δ 7.66 (d, J=9.0, 2H), 7.55 (s, 1H), 7.08 (d, J=9.0, 2H), 6.57–6.51 (m, 3H), 3.38 (s, 3H).

4-(3,4-Difluorophenoxy)benzaldehyde 2'-methylsemicarbazone, mp 170–171° C., $^1$H NMR (CDCl$_3$): δ 7.63 (d, J=8.7, 2H), 7.53 (s, 1H), 7.20–7.10 (m, 1H), 7.01 (d, J=9.0, 2H), 6.91–6.84 (m, 1H), 6.80–6.81 (m, 1H), 3.37 (s,3H).

4-(2,4-Difluorophenoxy)benzaldehyde 2'-methylsemicarbazone, mp 185–189° C., $^1$H NMR (CDCl$_3$): δ 7.59 (d, J=9.0 2H), 7.52 (s. 1H), 7.16–7.08 (m, 1H), 7.01–6.89 (m, 4H), 3.36 (s, 3H).

4(4-Chloro-2-fluorophenoxy)benzaldehyde 2'-methylsemicarbazone, mp 170–175° C., $^1$H NMR (CDCl$_3$): δ 7.61 (d, J=9.0, 2H), 7.52 (s, 1H), 7.27–7.02 (m, 3H), 6.98 (d, J=8.7, 2H), 3.36 (s, 3H).

5,6,7,8-Tetrahydro-2-naphthoxybenzaldehyde 2'-methylsemicarbazone, mp 120–124° C., $^1$H NMR (CDCl$_3$): δ 7.58 (d, J=8.4, 2H), 7.52 (s, 1H), 7.07–6.97 (m, 3H), 6.81–6.76 (m, 2H), 3.36 (s, 3H).

4-(4-Fluorophenoxy)-3-fluorobenzaldehyde 2'-methylsemicarbazone, mp 169–172° C., $^1$H NMR (CDCl$_3$): δ 7.50 (d, J=11, 1H), 7.47 (s, 1H), 7.29 (d, J=8.4 1H), 7.08–6.95 (m, 5H), 3.36 (s, 3H).

2-(4-Fluorophenoxy)-4-fluorobenzaldehyde 2'-methylsemicarbazone, mp 173–175° C., $^1$H NMR (CDCl$_3$): δ 7.90 (d, J=7.8, 1H), 7.87 (s, 1H), 7.30 (d, J=8.1, 1H), 7.14 (t, J=7.5, 1H), 7.08–6.94 (m, 4H), 6.83 (d, J=8.4, 1H), 3.31 (s, 3H).

4-(4-Fluorophenoxy)-2-fluorobenzaldehyde 2'-methylsemicarbazone, mp 122–125° C.

2,6-Difluoro-4-(4-fluorophenoxy)benzaldehyde 2'-methylsemicarbazone, mp 135–136° C., $^1$H NMR (CDCl$_3$): δ 7.67 (s, 1H), 7.09–7.00 (m, 6H), 3.29 (s, 3H).

4-(2,4,6-Trimethylphenoxy)benzaldehyde 2'-methylsemicarbazone, mp 165–167° C., $^1$H NMR (CDCl$_3$): δ 7.54 (s, 1H), 7.51 (d, J=4.2, 2H), 6.91 (s, 2H), 6.78 (d, J=8.7, 2H), 3.34 (s, 3H), 2.31 (s, 3H), 2.08 (s, 6H).

4-(3,4-Methylenedioxyphenoxy)-3-fluorobenzaldehyde 2'-methylsemicarbazone, mp 149–151° C., $^1$H NMR (CDCl$_3$): δ 7.50 (d, J 9.9, 1H), 7.47 (s, 1H), 6.95 (t, J=8.7, 1H), 6.76 (d, J=8.4, 1H), 6.60 (d, J=2.4, 1H), 6.51–6.48 (m, 1H), 5.99 (s, 2H), 3.35 (s, 3H).

3-Fluoro-4-(5-indanoxy)benzaldehyde 2'-methylsemicarbazone, mp 140–145° C., $^1$H NMR (CDCl$_3$): δ 7.52–7.45 (m, 2H), 7.28–7.28 (m, 1H), 7.18 (d, Jj=8.4, 1H), 6.98 (t, J=10.2, 1H), 6.88 (s, 1H), 6.81 (d, J=9.9, 1H), 3.36 (s, 3H), 2.89 (t, J=7.5, 4H), 2.13–2.08 (m, 2H).

3-Chloro-4-(4-fluorophenoxy)benzaldehyde 2'-methylsemicarbazone, mp 203–204° C., $^1$H NMR (CDCl$_3$): δ 7.77 (d, J=2.1, 1H), 7.45 (s, 1H), 7.42 (d, J=8.4, 1H), 7.09–6.96 (m, 4H), 6.89 (d, J=8.4, 1H), 3.36 (s, 3H).

3-Chloro4-(4-fluorophenoxy)benzaldehyde 2'-methylsemicarbazone, mp 147–150° C., $^1$H NMR (CDCl$_3$): δ 7.85 (s, 1H), 7.82 (d, J=2.7, 1H), 7.08–6.95 (m, 4H), 6.67 (d, J=9.0, 1H), 6.43 (d, J=2.7, 1H), 3.30 (s, 3H).

4-(4-Fluorophenoxy)-2-Trifluoromethylbenzaldehyde 2'-methylsemicarbazone, mp, $^1$H NMR (CDCl$_3$): δ 7.98 (d, J=9.3, 1H), 7.78 (s, 1H), 7.13–7.02 (m, 6H), 3.37 (s, 3H).

3-Chloro-4-(4-fluorophenoxy)benzaldehyde semicarbazone, mp 204–208° C., $^1$H NMR (DMSO-d$_6$): δ 10.3 (s, 1H), 8.09 (d, J=1.8, 1H), 7.78 (s, 1H), 7.57 (d, J=8.7, 1H), 7.28 (t, J=9.0, 2H), 7.07–7.02 (m, 2H), 6.97 (d, J=8.7, 1H), 6.65 (bs, 2H).

2-Chloro-4-(4-fluorophenoxy)benzaldehyde semicarbazone, mp 210–213° C., $^1$H NMR (DMSO-d$_6$): δ 10.20 (s, 1H), 8.13 (d, J=9.0, 1H), 8.07 (s, 1H), 7.12–7.04 (m, 4H), 6.73 (d, J=8.1, 1H), 6.45 (bs, 2H), 6.35 (s, 1H).

4-(4-Fluorophenoxy)-2-Trifluoromethylbenzaldehyde semicarbazone, mp 182–185° C., $^1$H NMR (DMSO-d$_6$): δ 10.48 (s, 1 H), 8.40 (d, J=9.3, 1H), 7.29–7.20 (m, 6H), 6.57 (bs, 2H).

2-(4-Fluorophenoxy)-4-fluorobenzaldehyde semicarbazone, 176–180° C., $^1$H NMR (DMSO-d$_6$): δ 9.23 (s, 1H), 7.56 (d, J=8.7, 1H), 7.24–7.00 (m, 5H), 6.70 (d, J=8.4, 1H), 6.42 (d, J=2.4, 1H), 6.24 (bs, 2H).

4-(2-Chloro-4-fluorophenoxy)benzaldehyde semicarbazone, mp 196–199° C., $^1$H NMR (DMSO-d$_6$): δ 10.17 (s, 1H), 7.78 (s, 1H), 7.70 (d, J=8.4, 2H), 7.63 (d, J=7.5, 1H), 7.26 (d, J=6.3, 2H), 6.89 (d, J=8.4, 2H), 6.44 (s, 2H).

4-(4-Chlorophenoxy)benzaldehyde semicarbazone, mp 219–221 ° C., $^1$H NMR (DMSO-d$_6$): δ 10.19 (s, 1H), 7.80 (s, 1H), 7.73 (d, J=9.0, 2H), 7.43 (d, J=9.0, 2H), 7.05 (d, J=8.7, 2H), 7.00 (d, J=9.0, 2H), 6.45 (bs, 2H).

4-(3,5-Difluorophenoxy)benzaldehyde semicarbazone, mp 186–191° C., $^1$H NMR (DMSO-d$_6$): δ 10.23 (s, 1H), 7.82 (s, 1H), 7.77 (d, J=8.4, 2H), 7.10 (d, J=8.1, 2H), 7.06–6.96 (m, 1H), 6.76 (d, J=6.6, 2H), 6.47 (bs, 2H).

4-(2,4-Difluorophenoxy)benzaldehyde semicarbazone, mp 220–223° C., $^1$H NMR (DMSO-d$_6$): δ 10.17 (s, 1H), 7.78 (s, 1H), 7.69 (d, J=8.7, 2H), 7.49 (m, 1H), 7.33 (m, 1H), 7.14 (m, 1H), 6.93 (d, J=8.1, 2H), 6.43 (bs, 2H).

4-(2-Fluoro-4-chlorophenoxy)benzaldehyde semicarbazone, mp 218–220° C., $^1$H NMR (DMSO-d$_6$): δ 10.19 (s, 1H), 7.79 (s, 1H), 7.37–7.63 (m, 3H), 7.30–7.23 (m, 2H), 6.98 (d, J=7.8, 2H), 6.44 (bs, 2H).

2-Fluoro-4-(4-fluorophenoxy)benzaldehyde semicarbazone, mp 217–219° C., $^1$H NMR (DMSO-d$_6$): δ 10.21 (s, 1H), 8.13 (d, J=8.4, 1H), 8.07 (s, 1H), 7.24–7.18 (m, 4H), 6.74 (d, J=9.6, 1H), 6.45 (bs, 2H), 6.36 (s, 1H).

EXAMPLE 32

4-(3-Octoxy)benzaldehyde semicarbazone and 4-(3-Octoxy)benzaldelyde 2'-methylsemicarbazone a) 4-(3-octoxy)benzaldehyde.

A solution of 3-bromooctane (792 mg, 0.41 mmol), 4-hydroxylbenzaldehyde (948 mg, 0.776 mmol), and potassium carbonate in N,N-dimethylacteamide (30 mL) were refluxed for 17 hours. The reaction was allowed to cool to rt, then diluted with hexane/ethylacetate (1:1 ratio, 100 mL), washed with water (80 mL), aqueous sodium hydroxide (2N, 100 mL), brine (100 mL), dried over sodium sulfate, and finally concentrated under reduce pressure to give a yellow liquid (0.33 g, 34% yield). $^1$H NMR (CDCl$_3$): δ 4.1–3.9 (m, 1H), 1.95–1.20 (m, 10H), 1.00–0.81 (m, 6H).

b) 4-(3-Octoxy)benzaldehyde semicarbazone.

This molecule was prepared as described for 4-(4-fluoro-2-chlorophenoxy)benzaldehyde semicarbazone, mp 45° C., $^1$H NMR (DMSO-d$_6$): δ 10.05 (s, 1H), 7.74 (s, 1H), 7.59 (d, J=8.1, 2H), 6.89 (d, J=8.7, 2H), 6.38 (bs, 2H), 4.32–4.28 (m, 1H), 1.59–1.52, 1.24–1.19, 0.90–0.82 (m, 1H).

c) 4-(3-Octoxy)benzaldehyde 2'-methylsemicarbazone.

This molecule was prepared as described for 4-(4-methylphenoxy)benzaldehyde 2'-methylsemicarbazone, mp 45° C., $^1$H NMR (DMSO-d$_6$): δ 7.72 (d, J=8.7, 2H), 7.60 (s, 1H), 6.91 (d, J=9.0, 2H), 6.68 (bs, 2H), 4.32–4.29 (m, 1H), 3.19 (s, 3H), 1.60–1.57 (m, 4H), 1.26 (bs, 7H), 0.91–0.83 (m, 5H).

The following molecules were synthesized as described for 4-(3-octoxy)benzaldehyde semicarbazone or 4-(3-octoxy)benzaldehyde 2'-methylsemicarbazone:

4-Cycloheptoxybenzaldehyde 2'-methylsemicarbazone, mp 165–169° C. $^1$H NMR (CDCl$_3$): δ 7.55 (d, J=9.0, 2H), 7.50 (s, 1H), 6.88 (d, J=9.0, 2H), 4.45 (m, 1H), 3.35 (s, 3H), 2.03–2.00 (m, 4H), 1.82–1.77 (m, 4H), 1.49 (m, 4H 4-(4-Nitrophenoxy)benzaldehyde 2'-methylsemicarbazone, mp 180–185° C.

4-Adamantanoxybenzaldehyde 2'-methylsemicarbazone, 162° C. $^1$H NMR (CDCl$_3$): δ 7.55 (d, J=9.0, 2H), 7.51 (s, 1H), 6.94 (d, J=8.7, 2H), 4.46 (s, 1H), 3.35 (s, 3H), 2.17, 1.90, 1.76 (bs, 12H).

4-(Diphenylmethoxy)benzaldehyde 2'-methylsemicarbazone, 141–145° C., mp 141–145° C., $^1$H NMR (CDCl$_3$): δ 7.51–7.26 (m, 13) 6.97 (d, J 9.0, 2H), 6.25 (s, 2H), 3.32 (s, 3H).

4-Triphenylmethoxybenzaldehyde semicarbazone, 139–142° C., $^1$H NMR (DMSO-d$_6$): δ 10.04 (s, 1H), 7.63 (s, 1H), 7.42–7.18 (m, 17H), 6.64 (d, J=9.0, 2H), 6.35 (bs, 2H).

4-(Diphenylmethoxy)benzaldehyde semicarbazone, 128° C. $^1$H NMR (DMSO-d$_6$): δ 10.06 (s, 1H), 7.70 (s, 1H), 7.56 (d, J=9.0, 2H), 7.48 (d, J=8.1, 4H), 7.36–7.24 (m, 4H), 7.18 (d, J=5.7, 2H), 7.00 (d, J=3.5, 2H), 6.57 (s. 1H), 6.37 (bs, 2H).

4-(exo-2-Norbornoxy)benzaldehyde 2'-methylsemicarbazone, 180–185° C. $^1$H NMR (CDCl$_3$): δ 7.54 (d, J=8.4, 2H), 7.50 (s, 1H), 6.88 (d, J=8.4, 2H), 4.60 (m, 1H), 2.6–1.2 (m, 10H).

4-(4-Tetrahydropyranoxy)benzaldehyde 2'-methylsemicarbazone, mp 185–186° C. $^1$H NMR (CDCl$_3$): δ 7.57 (d, J=8.4, 2H), 7.51 (s, 1H), 6.94 (d, J=9.0, 2H), 4.54 (m, 1H), 4.03–3.60 (m, 2H), 3.63–3.35 (m, 2H), 3.35 (s, 3H) 2.02 (m, 2H), 1.82 (m, 2H).

EXAMPLE 33

4-Benzylbenzaldehyde semicarbazone and 4-Benzylbenzaldelhyde 2'-methylsemicarbzone a) 4-Benzylbenzaldehyde.

A solution of (4-bromophenyl)phenylmethane (5.42 mmol) in 30 mL of dry THF at −78° C. was treated with nBuLi (4.4 mL of 1.6 M in hexane). After 1 h, N-formylpiperidine (5.94 mmol in THF) was added via syringe. The solution was stirred overnight and then evaporated under reduced pressure. Column chromatography gave the title product (1.74 g). $^1$H NMR (CDCl$_3$): δ 9.55 (s, 1H), 7.84 (d, 2H), 7.45–7.15 (m, 6H), 4.10 (s, 2H). $^1$H NMR (CDCl$_3$): δ 9.55 (s, 1H), 7.84 (d, 2H), 7.45–7.15 (m, 6H), 4.10 (s, 2H).

b) 4-Benzylbenzaldehyde semicarbazone was prepared as described for 4-(4-fluoro-2-chlorophenoxy)benzaldehyde semicarbazone. mp 118–120° C., $^1$H NMR (DMSO-d$_6$): δ 10.12 (s, 1H), 7.78 (s, 1H), 7.60 (d, J=7.5, 2H), 7.30–7.17 (m, 6H), 6.37 (bs, 2H), 3.94 (s, 2H).

c) 4-Benzylbenzaldehyde 2'-methylsemicarbzone was prepared as described for 4-(4-methylphenoxy)benzaldehyde 2'-methylsemicarbazone, mp 142–144° C., $^1$H NMR (CDCl$_3$): δ 7.56 (d, J=8.1, 2H), 7.30–7.12 (m, 6H), 4.00 (s, 2H), 3.35 (s, 3H).

EXAMPLE 34

4-(4-Trifluoromethylphenoxy)benzaldehiyde 2'-methlylsemicarbazone and 4-(4-Trifluoromethylphenoxy)benzalaldehyde semicarbazone a) 4-(4-Trifluoromethylphenoxy)benzaldehyde.

Trifluoro-p-cresol (1.608 g, 0.992 mmol) was dissolved in anhydrous THF (20 mL) at 0° C. The solution was purged with nitrogen for 10 minutes. Sodium hydride (60% in dispersion oil, 0.522 g, 13.0 mmol) was added to the solution. The solution was stirred at 0° C. for 50 minutes, then the ice bath was removed. 4-Fluorobenzaldehyde was then added (0.925 mL, 8.60 mmol). The solution was stirred overnight. The solution was diluted with hexane/ethylacetate (1:1 ratio, 60 mL), washed with water, aqueous sodium hydroxide (2 N, 50 mL), brine, and dried over sodium sulfate. The organic layer was evaporated under reduce pressure to give solid product (0.570 g, 22% yield).

b) 4-(4-Trifluoromethylphenoxy)benzaldehyde 2'-methylsemicarbazone.

The title compound was prepared as described for 4-(4-methylphenoxy)benzaldehyde 2'-methylsemicarbazone, mp 156–159° C., $^1$H NMR (CDCl$_3$): δ 7.65–7.60 (m, 4H), 1.52 (s, 1H), 7.09 (t, J=8.4, 2H), 3.36 (s, 3H).

c) 4-(4-Trifluoromethylphenoxy)benzaldehyde semicarbazone.

The title compound was prepared as described for 4-(4-fluoro-2-chlorophenoxy)benzaldehyde semicarbazone, mp 119–122° C., $^1$H NMR (DMSO-d$_6$): δ 10.21 (s, 1H), 7.80–7.74 (m, 5H), 7.20 (t, J=7.8, 4H), 6.48 (bs, 2H).

EXAMPLE 35

4-(4-Fluorophenoxy)benzaldehyde 2'-(carbamylmethlyl)semicarbazone 4-(4-Fluorophenoxy)benzaldehyde semicarbazone (0.674 g, 2.47 mmol) and sodium hydride (60% in dispersion oil, 104 mg, 2.60 mmol) were added to DMF (30 mL) giving a yellow solution. After 10 min, 2-bromoacetamide (0.693 g, 5.00 mmol) was added. When the reaction had decolorized, ethyl acetate (150 mL) was added and the reaction was washed with water (3×). The organic layer was separated and concentrated to give a solid. The crude product was purified by column chromatography to give 100 mg (12%) of the title compound, mp 219–223° C. $^1$H NMR (DMSO-d$_6$): δ 7.79 (d, J=7.5, 2H), 7.45 (s, 2H), 7.24 (t, J=8.1, 2H), 7.113 (m, 2H), 6.95 (d, J=8.1, 2H), 4.49 (s, 2H).

The following compounds were prepared similarly:

4-(4-Fluorophenoxy)benzaldehyde 2'-(3-cyanopropyl)semicarbazone, mp 167–178° C. $^1$H NMR (CDCl$_3$): δ 7.59 (d, J=9.6, 3H), 7.06–6.96 (m, 6H), 4.11 (t, J=6.6, 2H), 2.46 (t, J=7.2, 2H), 2.04–1.96 (m, 2H).

4-(4-Fluorophenoxy)benzaldehyde 2'-(2-propynyl)semicarbazone, mp 141–142° C. $^1$H NMR (DMSO-d$_6$): δ 7.86 (d, J=8.7, 2H), 7.76 (s, 1H), 7.24 (t, J=9.0, 2H), 7.12–7.08 (m, 4H), 6.97 (d, J=8.7, 2H), 6.80 (bs, 2H) 4.72 (s, 2H).

4-(4-Fluorophenoxy)benzaldehyde 2'-(2-ethoxycarbonylmethyl)semicarbazone: mp 147–149° C., $^1$H NMR (DMSO-d$_6$): δ 7.82 (d, J=8.4, 2H), 7.55 (s, 1H), 7.24 (t, J=8.7, 2H), 7.12–7.07 (m, 2H), 6.96 (d, J=8.4, 2H 6.80 (bs, 2H), 4.72 (s, 2H), 4.15–4.08 (m, 2H), 1.19 (t, J=6.9, 3H).

4-(4-Fluorophenoxy)benzaldehyde 2'-(2-propenyl)semicarbazone, mp 134–135° C. $^1$H NMR (DMSO): δ 7.80 (d, J=8.7, 2H), 7.56 (s, 1H), 7.23 (t, J=8.7, 2H), 7.10–7.06 (m, 2H), 6.94 (d, J=8.4, 2H), 6.69 (bs, 2H), 5.78–5.74 (m, 1H), 5.10 (d, J=10.2, 1H), 4.99 (d, j=17.1, 1H), 4.53 (s, 2H).

4-(4-Fluorophenoxy)benzaldehyde 2'-benzylsemicarbazone, mp 182–183° C. $^1$H NMR (DMSO): δ 7.72 (d, J=7.8, 2H), 7.56 (s, 1H), 7.31 (t, J=7.2, 3H), 7.22 (m, 4H), 7.08–7.05 (m, 2H), 6.90 (d, J=7.2, 2H), 5.15 (s, 2H).

EXAMPLE 36

4-(4-Fluorophenoxy)benzaldehyde semicarbazone as Na$^+$ Channel Blocker 4-(4-Fluorophenoxy)benzaldehyde semicarbazone was tested in the electrophysiological and binding assays described above and produced dose-dependent inhibition of voltage-gated Na$^+$ currents recorded in acutely dissociated rat hippocampal neurons. The blocking effect of this compound on Na$^+$ currents was highly sensitive to the holding voltage. For example, at concentrations between 0.1–10 μM, 4-(4-fluorophenoxy)benzaldehyde semicarbazone had very little effect on Na$^+$ currents activated from a holding membrane voltage of −100 mV, but inhibited currents with increasing potency as the holding potential was progressively depolarized.

Table 1 presents the $IC_{50}$ values derived from concentration-inhibition curves for the captioned compound taken at different holding voltages. The most potent block in these studies was seen at a membrane holding voltage of −60 mV. At this holding voltage the $Na^+$ current was decreased by 65% as compared to currents elicited from a holding voltage of −100 mV. The decrease in current was due to steady-state inactivation of the $Na^+$ channels. There was a direct correlation between inhibitory potency of the captioned compound and the degree of $Na^+$ channel inactivation (Table 1): the higher the degree of inactivation the higher the potency of antagonism. 4-(4 Fluorophenoxy)benzaldehyde semicarbazone appeared to have little effect on the overall shape of the $Na^+$ channel current-voltage relationship measured at peak current.

This data indicates that 4-(4-fluorophenoxy)benzaldehyde semicarbazone binds to voltage-sensitive $Na^+$ channels in their inactivated states and has weak potency towards $Na^+$ channels in their resting states (Ragsdale et al., *Mol. Pharmacol.* 40:756–765 (1991); Kuo and Bean, *Mol. Pharmacol.* 46:716–725 (1994)). The apparent antagonist dissociation constant ($K_d$) of this compound for inactivated $Na^+$ channels is ~0.6 $\mu$M.

TABLE 1

Relationship between holding potential, potency of $Na^+$ current inhibition by 4-(4-fluorophenoxy)benzaldehyde semicarbazone, and level of $Na^+$ current inactivation.

| HOLDING POTENTIAL (MV) | $IC_{50}$ (MM) | $NA^+$ CURRENT INACTIVATION % |
|---|---|---|
| −100 | >30 | 0 |
| −90 | 25 | 2 |
| −80 | 4.9 | 8 |
| −70 | 2.2 | 25 |
| −60 | 1 | 65 |

TABLE 2

Modulation of site 1 and site 2 of $Na^+$ channel by 4-(4-fluorophenoxy)benzaldehyde semicarbazone (Compound A).

| $NA^+$ CHANNEL | COMPOUND | $IC_{50}$ |
|---|---|---|
| Site 1 | Tetrodotoxin | 12 nM |
|  | Lidocaine | >100 $\mu$M |
|  | Compound A | >100 $\mu$M |
| Site 2 | Tetrodotoxin | >100 $\mu$M |
|  | Lidocaine | 29.9 $\mu$M |
|  | Compound A | 22 $\mu$M |

EXAMPLE 37

Antinociceptive Activity of 4-(4-Fluorophenoxy) benzaldeiyde semicarbazone

Analgesic activity of 4-(4-fluorophenoxy)benzaldehyde semicarbazone was assessed in the formalin test. The method of Hunskaar, et al., *J. Neurosci. Method* 14:69–76 (1985), was used with some modifications as described in the following.

Mice were placed in Plexiglas jars for at least 1 h to accommodate to experimental conditions. Following the accommodation period, mice were weighed and injected with 4-(4-Fluorophenoxy)benzaldehyde semicarbazone by i.p. or p.o. administration. Control mice were injected with saline (10 ml/kg). Fifteen min (i.p.) or 30 min (p.o.) following 4-(4-fluorophenoxy)benzaldehyde semicarbazone administration mice were injected with formalin (20 ml of 5% formaldehyde solution in saline) into the dorsal surface of the right hand paw. Mice were immediately transferred to the Plexiglas jars and the amount of time that each mouse spent licking and/or biting the injected paw was recorded for every 5-min period over the 1 h observation period. The data presented here are at 0–5 min (early phase) and from 5–60 min (late phase) following formalin injections. The late phase of the formalin test is the average of eleven 5-min periods.

Figure 1B:
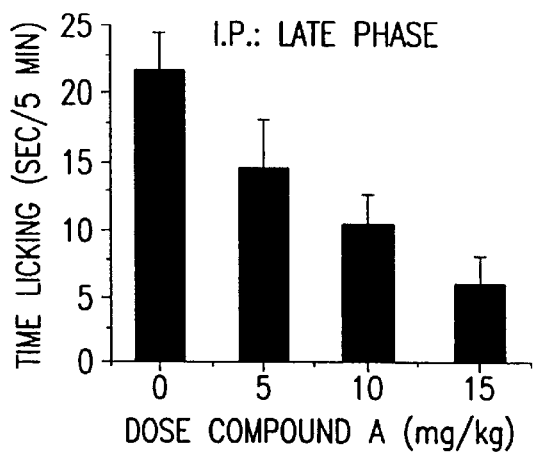
Figure 1C:
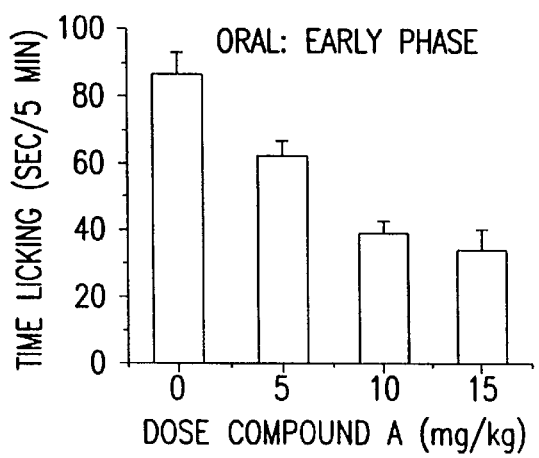
FIGS. 1C and 1D are graphs of the antinociceptive effects (time licking) of a compound of the present invention as a function of oral doses of said compound. The effects were measured in the formalin test in mice as described herein.
Figure 1D:
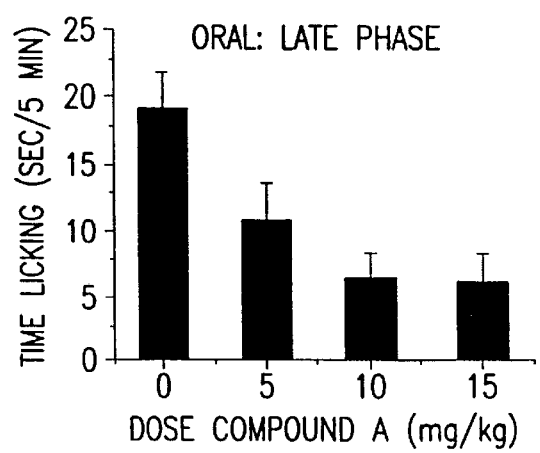

The result of this test are shown in FIG. 1. The antinociceptive activity of 4-(4-fluorophenoxy)benzaldehyde semicarbazone is demonstrated. The compound has a potency of $ED_{50}$ about 5–10 mg/kg by both routes of administration.

EXAMPLE 38

4-(3,4-Methylenedioxyphenoxy)benzaldehyde semicarbazone as anticonvulsant

The ability of 4-(3,4-methylenedioxyphenoxy) benzaldehyde semicarbazone to block maximal electroshock-induced seizures (MES) was determined by the following procedure.

Seizures were induced by application of current (50 mA, 60 pulses/sec, 0.8 msec pulse width, 1 sec duration, D.C.) using a Ugo Basile ECT device (model 7801). Mice were restrained by gripping the loose skin on their dorsal surface and saline-coated corneal electrodes were held lightly against the two cornea. Current was applied and mice were observed for a period of up to 30 sec for the occurrence of a tonic hindlimb extensor response. A tonic seizure was defined as a hindlimb extension in excess of 90 degrees from plane of the body.

4-(3,4-Methylenedioxyphenoxy)benzaldehyde semicarbazone was administered orally to mice 30 min before the test procedure. The compound exhibited protection against MES with an $ED_{50}$ (the dose provided protection of 50% of animals) of 5.3 mg/kg.

Additional compounds of the present invention were further tested in vitro and in vivo and the results are presented in Table 3. The relative in vitro potency of these compounds were determined by their ability to inhibit human skeletal muscle $Na^+$ channel subunit stable expressed in HEK-293 cells. The techniques employed for $Na^+$ current recordings and analysis with the use of this cell line were similar to that described in example 36. These studies employ depolarizing prepulses of varying duration to allow drugs to bind, a brief (5 ms) repolarizing step to reprime unbound channels, followed by the test pulse (5 ms) to measure what proportion of channels are inhibited. The reduction in peak currents is then plotted as a function of prepulse duration and the time constant ($\tau$) measured by monoexponential fit. A plot of $1/\tau$ as a function of antagonist concentration then allows the macroscopic binding rates of the antagonists to be calculated. The anticonvulsant activities of additional compounds of the present invention were determined as described in example Table 38.

TABLE 3

| Compound Name | $HsmNa^+$ Ki ((M) | MES ($ED_{50}$ mg/kg) |
|---|---|---|
| 4-(2-pyrimidinoxy)benzaldehyde semicarbazone | 1.1 |  |
| 4-cycloheptoxybenzaldehyde semicabazone | 0.25 | 3.2 |
| 4-(5-indanoxy)benzaldehyde semicarbazone | 0.04 | 1.7 |

TABLE 3-continued

| Compound Name | HsmNa+ Ki ((M) | MES (ED$_{50}$ mg/kg) |
|---|---|---|
| 3-fluoro-4-(4-fluorophenyl)benzaldehyde semicarbazone | 0.68 | 3 |
| 4-(4-fluorophenoxy)benzaldehyde semicarbazone | 0.21 | 1.6 |
| 4-(4-butoxyphenoxy)benzaldehyde semicarbazone | 6 | 14.9 |
| 4-(3,4-methylenedioxyphenoxy)benzaldehyde semicarbazone | 0.67 | 3.4 |
| 3-[4-(4-Fluorophenoxy)phenyl]methylene] aminooxazolidin-2-one | 67 | |
| 4-(4-fluorophenyl)benzoylsemicarbazide | 70 | |
| 4-(3,4-difluorophenoxy)benzaldehyde semicarbazone | 0.2 | |
| 4-(2-fluoro-4-chlorophenoxy)benzaldehyde semicarbazone | 0.06 | |
| 4-(4-fluorothiophenoxy)benzaldehyde semicarbazone | 0.13 | |
| lamotrigine | 16 | |
| 4-(4-fluorophenyl)benzaldehyde 2'-methylsemicarbazone | 0.15 | 1.5 |
| 2-[4-(3-fluorobenzyloxy)benzylamino]-2-methylpropanamide | 0.4 | |
| 4-(4-fluorophenoxy)phenylmethylsemicarbazide | 7.5 | 4.2 |
| 4-(4-fluorophenoxy)-3-fluorobenzaldehyde 2'-methylsemicarbazone | 0.15 | 0.9 |
| 2'-methyl-4-(4-fluorophenoxy)phenylmethylsemicarbazide | 16 | 3.2 |

Having now fully described this invention, it will be understood by those of ordinary skill in the art that the same can be performed within a wide and equivalent range of conditions, formulations and other parameters without affecting the scope of the invention or any embodiment thereof. All patents and publications cited herein are fully incorporated by reference herein in their entirety.

What is claimed is:

1. A method for treating, preventing or ameliorating pain, comprising administering to a mammal in need of such a treatment an effective amount of a compound having the Formula I:

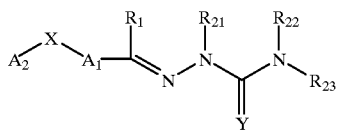

I or a pharmaceutically acceptable salt or prodrug thereof, wherein:

Y is oxygen or sulfur;

$R_1$, is hydrogen, alkyl, cycloalkyl, alkenyl, alkynyl, haloalkyl, aryl, aminoalkyl, hydroxyalkyl, alkoxyalkyl or carboxyalkyl;

$R_{21}$, $R_{22}$ and $R_{23}$ are independently hydrogen, alkyl, cycloalkyl, alkenyl, alkynyl, haloalkyl, aryl, aminoalkyl, hydroxyalkyl, alkoxyalkyl or carboxyalkyl, or $R_{21}$, is defined as above, and $R_{22}$ and $R_{23}$ together with the nitrogen atom to which they are attached form a heterocycle selected from the group consisting of piperidine, piperazine and morpholine;

$A_1$ and $A_2$ are independently aryl, heteroaryg, saturated or partially unsaturated carbocycle or saturated or partially unsaturated heterocycle, any of which is optionally substituted with one or more substituents selected from the group consisting of halo, haloalkyl, ary, heterocycle, cycloalkyl, heteroaryl, alkyl, alkenyl, alkynyl, arylalkyl, arylalkenyl, arylalkynyl, heteroarylalkyl, heteroarylalkenyl, heteroarylalkynyl, cycloalkylalkyl, heterocycloalkyl, hydroxyalkyl, aminoalkyl, carboxyalkyl, alkoxyalkyl, nitro, amino, ureido, cyano, acylamino, hydroxy, thiol, acyloxy, azido, alkoxy, carboxy, aminocarbonyl, and alkylthiol;

X is one of O, S, $NR_{24}$, $CR_{25}R_{26}$, C(O), $NR_{24}C(O)$, $C(O)NR_{24}$, SO, or $SO_2$; where $R_{24}$ is hydrogen, alkyl, cycloalkyl, alkenyl, alkynyl, haloalkyl, aryl, aminoalkyl, hydroxyalkyl, alkoxyalkyl or carboxyalkyl; and $R_{25}$, and $R_{26}$ are independently hydrogen, alkyl, cycloalkyl, alkenyl, alkynyl, haloalkyl, aryl, aminoalkyl, hydroxyalkyl, alkoxyalkyl or carboxyalkyl.

2. The method according to claim 1, wherein:

$A_1$ and $A_2$ are phenyl moieties, that are each independently optionally substituted by one or two substituents independently selected from the group consisting of halogen, $C_{1-6}$ alkyl, $C_{3-8}$ cycloalkyl, cyano, $C_{1-6}$ alkoxy and $C_{6-10}$ aryloxy;

Y is O;

$R_1$ is hydrogen, $C_{1-6}$ alkyl, $C_{3-8}$ cycloalkyl or $C_{6-10}$ aryl;

$R_{21}$, $R_{22}$ and $R_{23}$ are independently hydrogen or $C_{1-6}$ alkyl; and X is oxygen or sulfur.

3. The method of claim 1, wherein:

$A_1$ is an optionally substituted aryl group selected from the group consisting of phenyl and naphthyl, and $A_2$ is an optionally substituted heteroaryl or aryl group selected from the group consisting of pyridyl, pyrimidinyl, 1,3,5-triazinyl, furanyl, thiophenyl, naphthyl, quinolyl, 3,4-methylenedioxyphenyl, 3,4-ethylenedioxyphenyl, indanyl, tetrahydronaphthyl and quinoxalinyl.

4. The method of claim 1, wherein $A_1$ is an optionally substituted aryl group selected from the group consisting of phenyl or naphthyl, and $A_2$ is an optionally substituted carbocycle or heterocycle selected from the group consisting of cyclopentyl, cyclohexyl, cycloheptyl, piperidinyl, morpholinyl, pyrrolidinyl, tetrahydrofuranyl, tetrahydropyranyl, cyclohexenyl, adamantyl, exo-norbornyl and cyclopentenyl.

5. The method according to claim 1, wherein said compound is selected from the group consisting of:

4-phenoxybenzaldehyde semicarbazone;

4-(3,4-methylenedioxyphenoxy)benzaldehyde semicarbazone;

4-(4-fluorophenoxy)benzaldehyde semicarbazone;

4-(4-chlorophenoxy)benzaldehyde semicarbazone;

4-(4-bromophenoxy)benzaldehyde semicarbazone;

4-(4-methoxyphenoxy)benzaldehyde semicarbazone;

4-(4-trifluoromethylphenoxy)benzaldehyde semicarbazone;

4-(4-methylphenoxy)benzaldehyde semicarbazone;

4-(3,4-difluorophenoxy)benzaldehyde semicarbazone;

4-(4-chloro-2-fluorophenoxy)benzaldehyde semicarbazone;

4-(4-nitrophenoxy)benzaldehyde semicarbazone;

4-(3-methylphenoxy)benzaldehyde semicarbazone;

4-(4-t-butylphenoxy)benzaldehyde semicarbazone;

4-(4-propylphenoxy)benzaldehyde semicarbazone;

4-(4-s-butylphenoxy)benzaldehyde semicarbazone;
4-(4-bromophenoxy)acetophenone semicarbazone;
4-(4-fluorophenoxy)acetophenone semicarbazone;
4-(4-fluorophenoxy)-3-fluoroacetophenone semicarbazone;
4-(4-chlorophenoxy)acetophenone semicarbazone;
4-(4-bromophenoxy)propiophenone semicarbazone;
4-(4-fluorophenoxy)propiophenone semicarbazone;
4-(4-chlorophenoxy)propiophenone semicarbazone;
4-phenylmercaptobenzaldehyde semicarbazone;
4-(4-fluorophenylmercapto)benzaldehyde semicarbazone;
4-(4-chlorophenylmercapto)benzaldehyde semicarbazone;
4-cyclohexyloxybenzaldehyde semicarbazone;
4-cycloheptyloxybenzaldehyde semicarbazone;
4-(5-indanyloxy)benzaldehyde semicarbazone;
4-(6-quinolinyloxy)benzaldehyde semicarbazone;
4-(4-fluorophenoxy)-3-fluorobenzaldehyde semicarbazone;
4-(4-fluorophenoxy)cyclohexane-1-carboxaldehyde semicarbazone;
4-(tetrahydropyranyloxy)benzaldehyde semicarbazone;
4-(1-methyl-4-piperidinoxy)benzaldehyde semicarbazone;
4-(diphenylmethoxy)benzaldehyde semicarbazone;
4-(4-trifluoromethylphenoxy)benzaldehyde 2'-methylsemicarbazone;
4-(diphenylmethoxy) benzaldehyde 2'-methylsemicarbazone;
4-benzyl benzaldehyde 2'-methylsemicarbazone;
4-(5-indanyloxy)benzaldehyde 2'-methylsemicarbazone;
4-(3,4-methylenedioxyphenoxy)benzaldehyde 2'-methylsemicarbazone;
3-fluoro-4-(3,4-methylenedioxyphenoxy)benzaldehyde 2'-methylsemicarbazone;
4-(4-nitrophenoxy)benzaldehyde 2'-methylsemicarbazone;
4-(4-fluorophenoxy)-3-fluorobenzaldehyde 2'-methylsemicarbazone;
4-(4-fluorophenoxy)benzaldehyde 4'-methylsemicarbazone; and
4-(4-fluorophenoxy)benzaldehyde 2'-methylsemicarbazone.

6. The method according to claim 1, wherein said compound is selected from the group consisting of:
4-(2-pyridinoxy)benzaldehyde semicarbazone;
4-(3-pyridinoxy)benzaldehyde semicarbazone;
4-(4-pyridinoxy)benzaldehyde semicarbazone;
4-(4-chloro-2-pyridinoxy)benzaldehyde semicarbazone;
4-(2-pyrimidinoxy)benzaldehyde semicarbazone;
2-phenoxypyridine-5-carboxaldehyde semicarbazone;
2-(4-chlorophenoxy)pyridine-5-carboxaldehyde semicarbazone; and
2-(4-fluorophenoxy)pyridine-5-carboxaldehyde semicarbazone.

7. The method according to claim 5, wherein said compound is selected from the group consisting of:
4-phenoxybenzaldehyde semicarbazone;
4-(4-fluorophenoxy)benzaldehyde semicarbazone;
4-(4-chlorophenoxy)benzaldehyde semicarbazone;
4-(4-bromophenoxy)benzaldehyde semicarbazone; and
4-(4-methoxyphenoxy)benzaldehyde semicarbazone;
or a pharmaceutically acceptable salt thereof.

8. The method according to claim 7, wherein said conmpound is 4-phenoxybenzaldehyde semicarbazone or a pharmaceutically acceptable salt thereof.

9. The method according to claim 7, wherein said compound is 4-(4-fluorophenoxy)benzaldelhyde semicarbazone or a pharmaceutically acceptable salt thereof.

10. The method according to claim 7, wherein said compound is 4-(4-chlorophenoxy)benzaldehyde semicarbazone or a pharmaceutically acceptable salt thereof.

11. The method according to claim 5, wherein said compoutnd is selected from the group consisting of:
4-(4-trifluoromethylphenoxy)benzaldehyde semicarbazone;
4-(4-methylphenoxy)benzaldehyde semicarbazone;
4-(3,4-difluorophenoxy)benzaldehyde semicarbazone;
4-(4-chloro-2-fluorophenoxy)benzaldehyde semicarbazone; and
4-(4-nitrophenoxy)benzaldehyde semicarbazone;
or a pharmaceutically acceptable salt thereof.

12. The method according to claim 5, wherein said compound is selected from the group consisting of:
4-(3-methylphenoxy)benzaldehyde semicarbazone;
4-(4-t-butylphenoxy)benzaldehyde semicarbazone;
4-(4-propylphenoxy)benzaldehyde semicarbazone; and
4-(4-s-butylphenoxy)benzaldehyde semicarbazone;
or a pharmaceutically acceptable salt thereof.

13. The metlhod according to claim 5, wherein said compound is selected frorn the group consisting of:
4-(4-bromophenoxy)acetophenone semicarbazone;
4-(4-fluorophenoxy)acetophenone semicarbazone;
4-(4-chlorophenoxy)acetophenone semicarbazone,
4-(4-bromophenoxy)propiophenone semicarbazone;
4-(4-fluorophenoxy)propiophenone semicarbazone; and
4-(4-chlorophenoxy)propiophenone semicarbazone;
or a pharmaceutically acceptable salt thereof.

14. The method according to claim 5, wherein said compound is selected from the group consisting of:
4-phenylmercaptobenzaldehyde semicarbazone;
4-(4-fluorophenylmercapto)benzaldehyde semicarbazone; and
4-(4-chlorophenylmercapto)benzaldehyde semicarbazone;
or a pharmaceutically acceptable salt thereof.

15. The method according to claim 14, wherein said compound is 4-phenylmercaptobenzaldehyde semicarbazone or a pharmaceutically acceptable salt thereof.

16. The method according to claim 5, wherein said compound is selected from the group consisting of:
4-(4-fluorophenoxy)-3-fluorobelzaldehyde semicarbazone;
4-(4-fluorophenoxy)benzaldehyde 4'-methylsemicarbazone; and
4-(4-fluorophenoxy)benzaldehyde 2'-methylsemicarbazone;
or a pharmaceutically acceptable salt thereof.

17. The method according to claim 1, wherein said pain is one of neuropatic pain, surgical pain or chronic pain.

18. The method according to claim 17, wherein said pain is neuropathic pain.

19. The method according to claim 17, wherein said pain is surgical pain.

20. The method according to claim 17, wherein said pain is chronic pain.

21. The method according to claim 1, wherein said compounds are blockers of voltage-sensitive sodium channels having an $IC_{50}$ of about 100 nM or less in an electrophysiological assay.

22. The method according to claim 1, comprising administering the compound orally at a dose of 0.0025 to 50 mg/kg, or an equivalent amount of the pharmaceutically acceptable salt thereof, per day of the body weight of the mammal being treated.

23. The method according to claim 1, comprising administering the compound by intramuscular injection at a dose of 0.00125 to 25 mg/kg, or an equivalent amount of the pharynaceutically acceptable salt thereof, per day of the body weight of the mammal being treated.

24. The method according to claim 1, comprising administering the compound in an oral dose comprising from about 0.01 to about 50 mg of the compound.

25. The method according to claim 24, comprising administering the compound in an oral dose comprising from about 0.1 to about 10 mg of the compound.

26. The method according to claim 24, comprising administering the oral dose once daily as one or more tablets eaclh containing from about 0.1 to about 10 mg of the compound or its solvates.

27. The method according to claim 24, comprising administering the oral dose once daily as one or more tablets each containing from about 0.25 to 50 mg of the compound or its solvates.

28. The method according to claim 24, comprising administering the oral dose more than once daily as one or more tablets each containing from about 0.1 to about 10 mg of the compound or its solvates.

29. The metlhod according to claim 24, comprising administering the oral dose more than once daily as one or more tablets each containing from about 0.25 to about 50 mg of the compound or its solvates.

30. The method according to claim 1, comprising administering the compound by a parenteral route.

31. The method according to claim 1, comprising administering the compound by a subcutaneous route.

32. The method according to claim 1, comprising administering the compound by an intravenous route.

33. The methdod according to claim 1, comprising administering the compound by an intramuscular route.

34. The method according to claim 1, comprising administering the compound by an intraperitoneal route.

35. The method according to claim 1, comprising administering the compound by a transdermal route.

36. The method according to claim 1, comprising administering the compound by a buccal route.

37. The method according to claim 1, comprising administering the compound by a rectal route.

38. The method according to claim 1, wherein said one or more substituents are selected from the group consisting of halo, haloalkyl, hydroxyalkyl, aminoalkyl, nitro, alkyl, alkoxy, and amino.

* * * * *